United States Patent [19]

Pankiewicz et al.

[11] Patent Number: 5,658,890
[45] Date of Patent: Aug. 19, 1997

[54] C-NUCLEOSIDE ISOSTERE OF NICOTINAMIDE ADENINE DINUCLEOTIDE, ANALOGS THEREOF AND USE AS ANTI-CANCER AGENT

[75] Inventors: Krysztof W. Pankiewicz, Bronxville; Kyoichi A. Watanabe, Rye-Brook; Andrzej Zatorski, New York, all of N.Y.

[73] Assignee: Sloan-Kettering Institute for Cancer Research, New York, N.Y.

[21] Appl. No.: 422,065

[22] Filed: Mar. 30, 1995

Related U.S. Application Data

[63] Continuation-in-part of Ser. No. 75,746, Jun. 11, 1993, Pat. No. 5,569,650.
[51] Int. Cl.$^6$ .......................... A61K 31/70; C07H 23/00
[52] U.S. Cl. .......................... 514/43; 514/47; 536/26.24
[58] Field of Search .................... 514/47, 43; 536/26.24

[56] References Cited

U.S. PATENT DOCUMENTS

| | | | |
|---|---|---|---|
| 3,266,989 | 8/1966 | O'Hollaren | 514/47 |
| 4,008,363 | 2/1977 | Re et al. | 536/26.24 |
| 4,088,639 | 5/1978 | Zappelli et al. | 536/26.24 |
| 4,443,594 | 4/1984 | Buckmann | 536/26.24 |
| 4,950,602 | 8/1990 | Cooper | 435/184 |

FOREIGN PATENT DOCUMENTS

| | | |
|---|---|---|
| 3936802 | 5/1991 | Germany . |
| 0096610 | 5/1985 | Japan . |
| 2067096 | 3/1987 | Japan . |

OTHER PUBLICATIONS

Tonooka et al., "Synthesis of Isonicotinic Acid Hydrazide (INH)- and Isonicotinic Acid (INA)-Analogs of NAD," *Hokkaido Daigaku Meneki Kagaku Kenkyusho Kiyo*, 37, pp. 14–18(1977); *Chem. Abstr.*, 87(23), p. 221, Abstract No. 1789705e (1977); Only abstract supplied.

Fujisawa et al., "Application of Nicotinamide–Adenine Dinucleotide Analogs for Clinical Enzymology; Alcohol Dehydrogenase Activity in Liver Injury," *Clin. Chim. Acta*, 69(2), 251–257 (1976); *Chem. Abstr.*, 85(7), p. 212, Abstract No. 42681h (1976); Only abstract supplied.

Danenberg et al., "The Interaction of Liver Alcohol Dehydrogenase with Phenyl Adenine Dinucleotide, a Novel Analog of Pyridine Nucleotide Coenzymes," *J. Biol. Chem.*, 253(17), 5886–5887 (1978).

Riley et al., "Synthesis of 2-(β-D-Ribofuranosyl)pyrimidines, A New Class of C-Nucleosides," *J. Heterocyclic Chem.* 24, 955–964 (1987).

Pankiewicz et al.(I), "Synthesis of Isosteric Analogues of Nicotinamide Adenine Dinucleotide Containing C-Nucleotide of Nicotinamide or Picolinamide," *J. Medicinal Chem.*, 36(3), 1855–1859 (1993).

Goldstein et al.(I), "CNAD: A Potent and Specific Inhibitor of Alcohol Dehydrogenase," *J. Medicinal Chem.*, 37(3), 392–399 (1994).

Kandel et al., "Interaction of Fragment A from Diphtheria Toxin with Nicotinamide Adenine Dinucleotide," *J. Biol. Chem.*, 249(7), 2088–2097 (1974).

Favilla et al., "The Binding of 1,N$^6$–ethenoNAD to Bovine Liver Glutamate Dehydrogenase; Studies Using the Time–Correlated Single Photon Counting Fluorescence Technique," *Biochim. Biophys. Acta*, 870, 41–49 (1986).

Moss et al., "Stimulation of the Thiol–Dependent ADP–Ribosyl Transferase and NAD Glycohydrolase Activities of *Bordetella pertussis* Toxin by Adenine Nucleotides, Phospholipids, and Detergents," *Biochemistry*, 25(9), 2720–2725 (1986).

Yoshikawa et al., "A Novel Method for Phosphorylation of Nucleosides to 5'–Nucleotides," *Tett. Lett.*, 19, 5065–5068 (1967).

Pankiewicz et al.(II), "Efficient Synthesis of 5-(β-D-Ribofuranosyl)nicotinamide and Its α-Isomer," *J. Org. Chem.*, 53(15), 3473–3479 (1988).

Kabat et al.(I), "Nucleosides. CXLVIII. Synthesis of 6-(β-D-Ribofuranosyl)picolinamide. A Novel C–Nucleoside from D–Ribonolactone," *Chem. Pharm. Bull.*, 36(2), 634–640 (1988).

Kabat et al.(II), "Syntheses of 5-β-D-Ribofuranosylnicotinamide and Its N-Methyl Derivative. The Isosteric and Isoelectronic Analogues of Nicotinamide Nucleoside," *J. Med. Chem.*, 30(5), 924–927 (1987).

Goldstein et al. (II), "Dehydrogenase Binding by Tiazofurin Anabolites," *J. Med. Chem.*, 33(4), 1123–1127 (1990).

(List continued on next page.)

*Primary Examiner*—John Kight
*Assistant Examiner*—L. Eric Crane
*Attorney, Agent, or Firm*—John P. White

[57] ABSTRACT

This invention provides a compound having the structure:

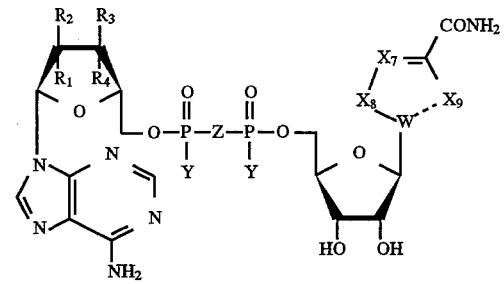

wherein each $R_1$, $R_2$, $R_3$, and $R_4$ is independently fluorine, OH or H; Z is O, $CH_2$ or $CF_2$; each Y is independently OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH.

This invention also provides a pharmaceutical composition comprising the compounds and methods of treating a mammal having an inosine monophosphate dehydrogenase associated disorder.

21 Claims, 1 Drawing Sheet

OTHER PUBLICATIONS

Kabat et al.(III), "Synthesis of C-Nucleoside Isosteres of Nicotinamide Nucleoside," Presentation at Am. Chem. Soc. Convention, Anaheim CA, Sep. 7–12, 1986, see abstract No. 89.

Kabat et al. (IV), "Synthesis of 5–Bromo–3–(ribofuranosyl)–pyridine," Presentation at Am. Chem. Soc. Convention, New York, NY, Apr. 13–18, 1986, see abstract No. 2.

Berger et al., "Modulation of Nicotinamide Adenine Dinucleotide and Poly(Adenosine Diphosphoribose) Metabolism by the Synthetic C Nucleoside Analogs, Tiazofurin and Selenazofurin," *J. Clinical Invest.*, 75(2), 702–709 (1985).

Gebeyehu et al., "Synthesis of Thiazolo–4–carboxamide Adenine Dinucleotide. A Powerful Inhibitor of IMP Dehydrogenase," *J. Medicinal Chem.*, 26(6), 922–925 (1983).

Gebeyehu et al., "Ribavirin, Tiazofurin, and Selenazofurin: Mononucleotides and Nicotinamide Adenine Dinucleotide Analogues. Synthesis, Structure, and Interactions with IMP Dehydrogenase," *J. Medicinal Chem.*, 28(1), 99–105 (1985).

Blackburn, G. M., et al., Synthesis and Resistance to Enzymic Hydrolysis of Sterochemically–Defined Phosphonate and Thiophosphate Analogues of P1, 4 P–bis (5'adenosyl) tetraphosphate. *Nucleic Acids Res.* (1987) 15(17): 6991–7004.

Bruzik, K. S., and Stec, W. J. (Eds.), Biophosphates and Their Analogues –Synthesis, Structure, Metabolism and Activity.

Feiser, M., *Reagents for Organic Synthesis* vol. 8. Published by Wiley & Sons (1980) (New York), p. 489.

Ikehara, M., et al., The Synthesis of Polynucleotides. *Advances in Carbohydrate Chemistry and Biochemistry* (1979) 36:180–192.

Klein, R. S., et al., Nucleosides. LXXIII. Ribosyl Analogs of Chloramphenicol. *J. Org. Chem.* (1971) 36(26): 4113–4116.

Tarussova, N. B., et al., Organophosphorous Analogues of Biologically Active Compounds. XIV. The Synthesis of P1, P4–bis(5'adenosyl) tetraphosphate and 5'–Nucleosidetriphosphate Phosphonate Analogues. *Biorganicheskaia Khimiia.* (1985) 11(6): 802–807.

$^{31}P$ NMR spectra of reaction of AMP with CDI a) 2 min.

AMP  $\delta = +1.75$
[A]  $\delta = -5.71$ b) 20 min.

[B]  $\delta = -6.10$
AMP-Imd  $\delta = -7.58$ c) 60 min.

$\delta = -7.76$ d) 2.5 h 2,3-O-Carbonyl-AMP-Imd

C-NUCLEOSIDE ISOSTERE OF NICOTINAMIDE ADENINE DINUCLEOTIDE, ANALOGS THEREOF AND USE AS ANTI-CANCER AGENT

The application is a continuation-in-part of U.S. Ser. No. 08/075,746, filed Jun. 11, 1993, now U.S. Pat. No. 5,569,650, the contents of which are herein incorporated by reference. The invention described herein was made in the course of work under Grant Nos. CA-45145, GM-42010 and CA 33907 from the National Cancer Institute and from National Institute of General Medical Sciences, National Institutes of Health, U.S. Department of Health and Human Services. The U.S. Government has certain rights in this invention.

BACKGROUND OF THE INVENTION

Throughout this application, various publications are referenced in Arabic numerals in parentheses. Full text citations of these publications can be found at the end of the specification, immediately preceding the claims. The disclosures of these publications in their entirety are hereby incorporated by reference into this application in order to more fully describe the state of the art as known to those skilled therein as of the date of the invention described and claimed herein.

The pyridine C-nucleoside having the structure:

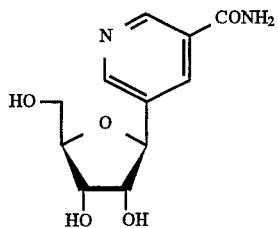

1 which is isosteric to nicotinamide riboside, was synthesized by these inventors [Kabat, Pankiewicz, Watanabe, *J. Med. Chem.*, 1987, 30, 924–927; Kabat et al., *Chem. Pharm. Bull.*, 1988, 36, 634–640; Pankiewicz et al., *J. Org. Chem.*, 1988, 53, 3473–3479] in the hope that such an analogue may be converted biologically into the corresponding nicotinamide adenine dinucleotide, NAD coenzyme, analog having the structure:

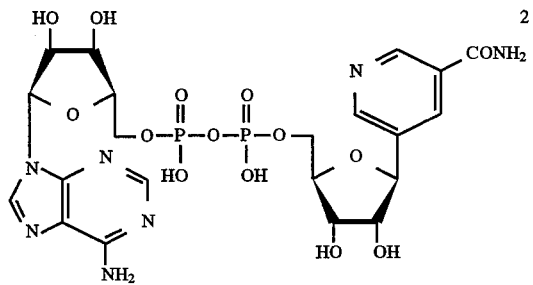

2 and exert biological activities. The non-charged NAD isostere, Compound 2, which is incapable of participating in biological oxidation-reduction process(es) may inhibit the NAD-dependent enzyme, IMP-dehydrogenase, and may induce anticancer activity by blocking the de novo GMP synthesis.

The NAD analog (Compound 2) which contains the C-nucleoside (Compound 1), was found to be a general competitive inhibitor (with respect to NAD) of various dehydrogenases such as inosine monophosphate dehydrogenase (IMPDH), glutamate dehydrogenase (GDH), lactate dehydrogenase (LDH) and malate dehydrogenase (MDH). Interestingly, the NAD analogue (Compound 2) exhibited highly potent and selective inhibitory activity against alcohol dehydrogenase from horse liver.

The present invention relates to the novel class of NAD analogs which contain the nicotinamide, picolinamide or isonicotinamide C-nucleoside in place of nicotinamide riboside. The compounds of this invention have the pyrophosphate (—P—O—P—) bridge connecting the nucleosides or, alternatively, can have a methylene diphosphonate (—P—CH$_2$—P—), or difluoromethylene diphosphonate (—P—CF$_2$—P—) group as the bridge.

Analogues that contain a methylene diphosphonate (—P—CH$_2$—P—) or difluoromethylene diphosphonate (—P—CF$_2$—P—) group in place of the pyrophosphate (—P—O—P—) bridge are resistant to enzymic hydrolysis to their corresponding nucleoside 5'-monophosphates. The 2'-fluoroinated adenosine analogues cannot be converted into the corresponding NADP analogues. Such analogues, therefore, cannot interfere with NADP dependent enzymes. In addition, fluorine substituted NAD analogues, as more lipophilic than their corresponding hydroxyl or pyrophosphate groups containing counterparts, could penetrate biological membranes and may better fit to the hydrophobic binding pocket of dehydrogenases.

The compositions of this invention are useful as potent inhibitors of various dehydrogenases of eucaryotic and procaryotic origin. These compounds may also be utilized as therapeutic agents exhibiting anticancer and antiviral activity.

Thiazole-4-carboxamide adenine dinucleotide (TAD) is the active metabolite of the oncolytic C-nucleoside, 2-(β-D-ribofuranosyl)thiazole-4-carboxamide (Tiazofurin, TR). TAD, an analogue of nicotinamide adenine dinucleotide (NAD), was found to be a potent inhibitor of inosine monophosphate dehydrogenase (IMPDH), the key enzyme in the de novo GTP biosynthesis and an important target in anticancer chemotherapy.(2–13) TAD mimics NAD but cannot function as the coenzyme. It has been discovered (14) recently that human IMPDH exists as two isoforms, type I and type II. In normal cells type I is the predominant isoenzyme while type II is selectively up-regulated in neoplastic cells and emerges as the dominant species. (15,16)

The goal in searching for antitumor agents based on IMPDH inhibition is, therefore, to develop a compound which would not affect numerous cellular dehydrogenases but would act as a selective inhibitor of IMPDH—type II.

SUMMARY OF THE INVENTION

This invention provides a compound having the structure:

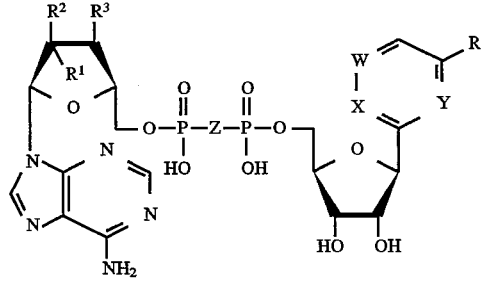

wherein $R^1$, $R^2$, and $R^3$ are same or different, and are hydrogen, hydroxyl, or fluorine; Z is O, CH$_2$ or CF$_2$; R is chlorine, bromine, iodine, carbonitrile, carboxylic ester, or carboxamide; and one of W, X and Y is N or N⁺R', wherein R' is methyl or ethyl, and all others are CH; provided that $R^1$ is not H when $R^2$ and $R^3$ are OH, Z is O, R is carboxamide and W is N or N⁺R'.

This invention also provides a compound having the structure:

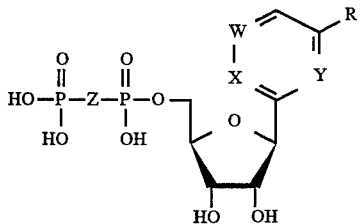

wherein Z is $CH_2$ or $CF_2$; R is chlorine, bromine, iodine, carbonitrile, carboxylic ester, or carboxamide; and one of W, X and Y is N or N⁺R', wherein R' is methyl or ethyl, and all others are CH.

This invention also provides a compound having the structure:

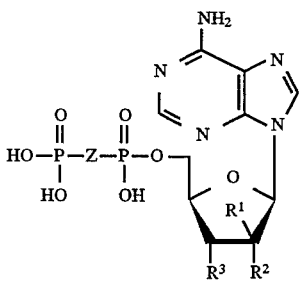

wherein Z is $CH_2$ or $CF_2$; and $R^1$, $R^2$, and $R^3$ are same or different, and are hydrogen, hydroxyl, or fluorine.

This invention also provides a pharmaceutical composition which comprises any of the above-identified compounds and a pharmaceutically acceptable carrier.

This invention further provides a method of treating a mammal having a NAD-dependent enzyme associated disorder which comprises administering to the mammal a pharmaceutically effective amount of a compound having the structure:

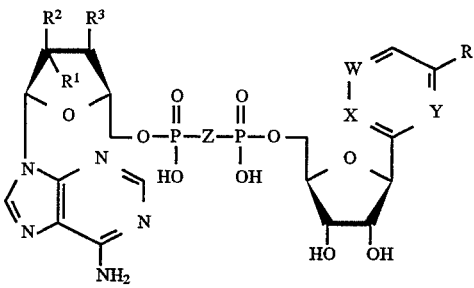

wherein $R^1$, $R^2$, and $R^3$ are same or different, and are hydrogen, hydroxyl, or fluorine; Z is O, $CH_2$ or $CF_2$; R is chlorine, bromine, iodine, carbonitrile, carboxylic ester, or carboxamide; and one of W, X and Y is N or N⁺R', wherein R' is methyl or ethyl, and all others are CH;
effective to inhibit the NAD-dependent enzyme, thereby treating the disorder.

This invention further provides methods of preparing the above-identified compounds.

The subject invention also provides a compound having the structure:

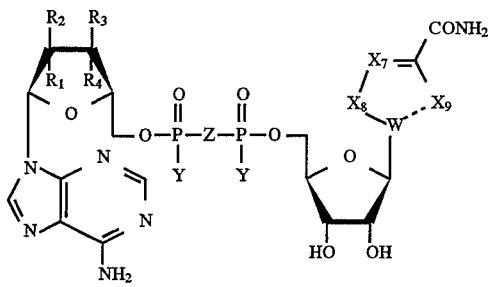

wherein each $R_1$, $R_2$, $R_3$, and $R_4$ is independently fluorine, OH or H; Z is O, $CH_2$ or $CF_2$; each Y is independently OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH.

The subject invention also provides a compound having the structure:

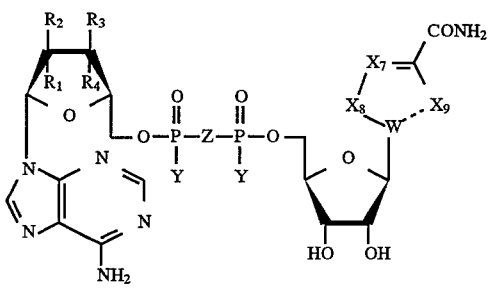

wherein one of $R_1$, $R_2$, $R_3$, and $R_4$ is fluorine, one is OH and the remainder are H; Z is O, $CH_2$ or $CF_2$; each Y is independently OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH.

The subject invention also provides a compound having the structure:

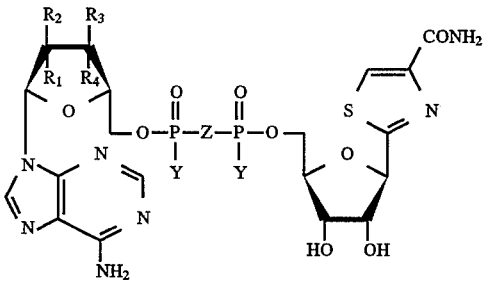

wherein one of $R_1$, $R_2$, $R_3$, and $R_4$ is fluorine, one is OH and the remainder are H; each Y is independently F or OH, and Z is O, $CH_2$ or $CF_2$.

The subject invention also provides a pharmaceutical composition which comprises any of the compounds defined above and a pharmaceutically acceptable carrier.

The subject invention provides a method of treating a mammal having an inosine monophosphate dehydrogenase associated disorder which comprises administering to the mammal a therapeutically effective amount of a compound having the structure:

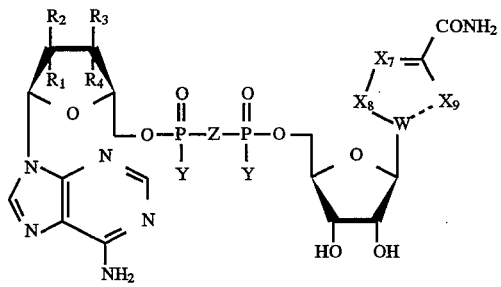

wherein each $R_1$, $R_2$, $R_3$, and $R_4$ is independently fluorine, OH or H; Z is O, $CH_2$ or $CF_2$; each Y is independently OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH.

The subject invention further provides a method of treating a mammal having an inosine monophosphate dehydrogenase associated disorder which comprises administering to the mammal a therapeutically effective amount of a compound having the structure:

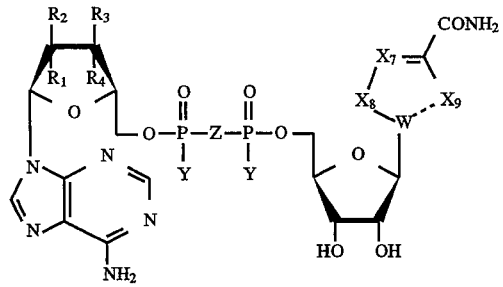

wherein one of $R_1$, $R_2$, $R_3$, and $R_4$ is fluorine, one is OH and the remainder are H; Z is O, $CH_2$ or $CF_2$; each Y is independently OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH;

effective to inhibit inosine monophosphate dehydrogenase, thereby treating the disorder.

The subject application further provides a pharmaceutical composition which comprises any of the above described compounds and a pharmaceutically acceptable carrier.

Finally, the subject invention also provides a method of treating a mammal having an inosine monophosphate dehydrogenase associated disorder which comprises administering to the mammal a therapeutically effective amount of a compound having the structure:

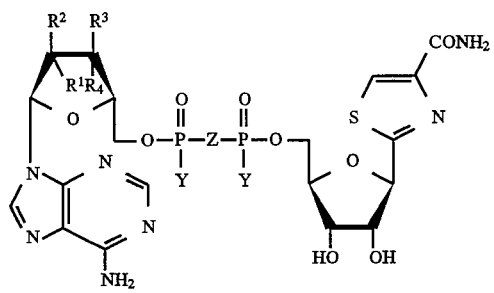

wherein one of $R_1$, $R_2$, $R_3$, and $R_4$ is fluorine, one is OH and the remainder are H; each Y is independently F or OH, and Z is O, $CH_2$ or $CF_2$;

effective to inhibit inosine monophosphate dehydrogenase thereby treating the disorder.

DETAILED DESCRIPTION

Figure 1:
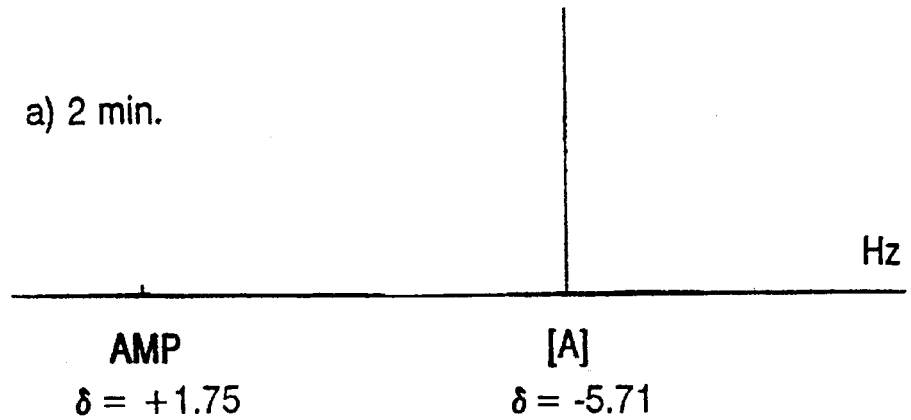
FIG. 1. $^{31}$P NMR spectra of reaction of AMP with CDI
Figure 1:
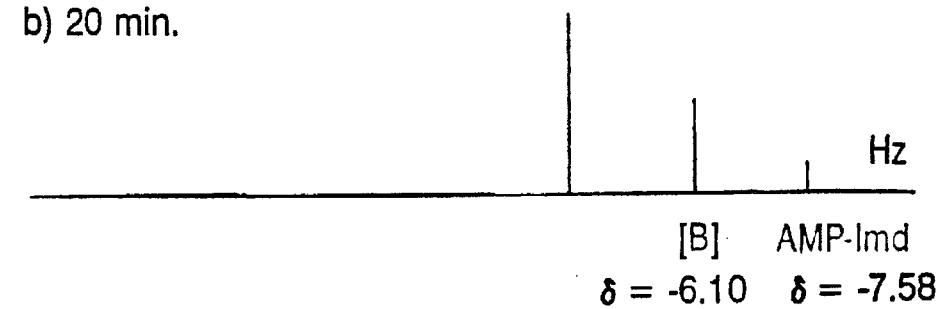
Figure 1:
Figure 1:
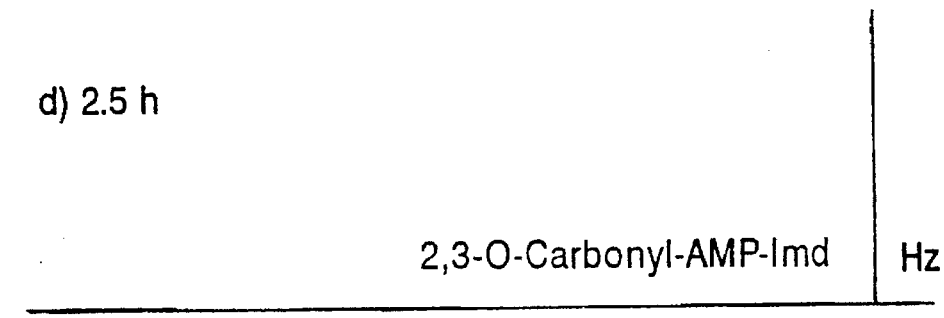

This invention provides a compound having the structure:

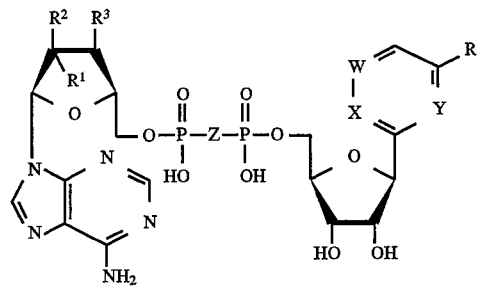

wherein $R^1$, $R^2$, and $R^3$ are same or different, and are hydrogen, hydroxyl, or fluorine; Z is O, $CH_2$ or $CF_2$; R is chlorine, bromine, iodine, carbonitrile, carboxylic ester, or carboxamide; and one of W, X and Y is N or $N^+R'$, wherein R' is methyl or ethyl, and all others are CH; provided that $R^1$ is not H when $R^2$ and $R^3$ are OH, Z is O, R is carboxamide and W is N or N¯R'.

Compounds having the above-identified structure, although not limited to the following compounds, may be selected from the group consisting of:

5-(β-D-Ribofuranosyl)nicotinamide-(5'-5")-adenosine pyrophosphate,
6-(β-D-Ribofuranosyl)picolinamide-(5'-5")-adenosine pyrophosphate,
2-(β-D-Ribofuranosyl)isonicotinamide-(5'-5")-adenosine pyrophosphate,
5-(β-D-Ribofuranosyl)-3-cyanopyridine-(5'-5")-adenosine pyrophosphate,
6-(β-D-Ribofuranosyl)-2-cyanopyridine-(5'-5")-adenosine pyrophosphate,
2-(β-D-Ribofuranosyl)-4-cyanopyridine-(5'-5")-adenosine pyrophosphate,
5-(β-D-Ribofuranosyl)nicotinamide-(5'-5")-2'-deoxyadenosine pyrophosphate,
6-(β-D-Ribofuranosyl)picolinamide-(5'-5")-2'-deoxyadenosine pyrophosphate,
2-(β-D-Ribofuranosyl)isonicotinamide-(5'-5")-2'-deoxyadenosine pyrophosphate,
5-(β-D-Ribofuranosyl)-3-cyanopyridine-(5'-5")-2'-deoxyadenosine pyrophosphate, 6-(β-D-Ribofuranosyl)-2-cyanopyridine-(5'-5")-2'-deoxyadenosine pyrophosphate, 2-(β-D-Ribofuranosyl)-4-cyanopyridine-(5'-5")-2'-deoxyadenosine pyrophosphate, 5-(β-D-Ribofuranosyl)nicotinamide-(5'-5")-2'-deoxy-2'-fluoroadenosine pyrophosphate, 6-(β-D-Ribofuranosyl)picolinamide-(5'-5")-2"-deoxy-2"-fluoroadenosine pyrophosphate, 2-(β-D-Ribofuranosyl)isonicotinamide-(5'-5")-2'-deoxy-2'-fluoroadenosine pyrophosphate, 5-(β-D-Ribofuranosyl)-3-cyanopyridine-(5'-5")-2'-deoxy-2'-fluoroadenosine pyrophosphate, 6-(β-D-Ribofuranosyl)-2-cyanopyridine-(5'-5")-2'-deoxy-2'-fluoroadenosine pyrophosphate, 2-(β-D-Ribofuranosyl)-4-cyanopyridine-(5'-5")-2'-deoxy-2'-fluoroadenosine pyrophosphate, 5-(β-D-Ribofuranosyl)nicotinamide-(5'-5")-3'-deoxy-3'-fluoroadenosine pyrophosphate, 6-(β-D-Ribofuranosyl)picolinamide-(5'-5")-3'-deoxy-3'-fluoroadenosine pyrophosphate, 2-(β-D-Ribofuranosyl)isonicotinamide-(5'-5")-3'-deoxy-3'-fluoroadenosine pyrophosphate, 5-(β-D-Ribofuranosyl)-3-cyanopyridine-(5'-5")-3'-deoxy-3'-fluoroadenosine pyrophosphate, 6-(β-D-Ribofuranosyl)-2-cyanopyridine-(5'-5")-3'-deoxy-3'-fluoroadenosine pyrophosphate, 2-(β-D-Ribofuranosyl)-4-cyanopyridine-(5'-5")-3'-deoxy-3'-fluoroadenosine pyrophosphate, 5-(β-D-Ribofuranosyl)nicotinamide-(5'-5")-9-(2'-deoxy-2'-fluoro-β-D-arabinofuranosyl)-adenine pyrophosphate, 6-(β-D-Ribofuranosyl)picolinamide-(5'-5")-9-(2'-deoxy-2'-fluoro-β-D-arabinofuranosyl)-adenine pyrophosphate, 2-(β-D-Ribofuranosyl)isonicotinamide-(5'-5")-9-(2'-deoxy-2'-fluoro-β-D-arabinofuranosyl)-adenine pyrophosphate, 5-(β-D-Ribofuranosyl)-3-cyanopyridine-(5'-5")-9-(2'-deoxy-2'-fluoro-β-D-arabinofuranosyl)-adenine pyrophosphate, 6-(β-D-Ribofuranosyl)-2-cyanopyridine-(5'-5")-9-(2'-deoxy-2'-fluoro-β-D-arabinofuranosyl)-adenine pyrophosphate, 2-(β-D-Ribofuranosyl)-4-cyanopyridine-(5'-5")-9-(2'-deoxy-2'-fluoro-β-D-arabinofuranosyl)-adenine pyrophosphate, $P^1$-[5-(β-D-Ribofuranosyl)nicotinamide-5'-yl]-$P^2$-[adenosine-5"-yl]methylenediphosphonate, $P^1$-[6-(β-D-Ribofuranosyl)picolinamide-5'-yl]-$P^2$-[adenosine-5"-yl]methylenediphosphonate, $P^1$-[2-(β-D-Ribofuranosyl)isonicotinamide-5'-yl]-$P^2$-[adenosine-5"-yl]methylenediphosphonate, $P^1$-[5-(β-D-Ribofuranosyl)-3-cyanopyridine-5'-yl]-$P^2$-[adenosine-5"-yl]methylenediphosphonate, $P^1$-[6-(β-D-Ribofuranosyl)-2-cyanopyridine-5'-yl]-$P^2$-[adenosine-5"-yl]methylenediphosphonate, $P^1$-[2-(β-D-Ribofuranosyl)-4-cyanopyridine-5'-yl]-$P^2$-[adenosine-5"-yl]methylenediphosphonate, $P^1$-[5-(β-D-Ribofuranosyl)nicotinamide-5'-yl]-$P^2$-[2'-deoxyadenosine-5"-yl]methylenediphosphonate, $P^1$-[6-(β-D-Ribofuranosyl)picolinamide-5'-yl]-$P^2$-[2'-deoxyadenosine-5"-yl]methylenediphosphonate, $P^1$-[2-(β-D-Ribofuranosyl)isonicotinamide-5'-yl]-$P^2$-[2'-deoxyadenosine-5"-yl]methylenediphosphonate, $P^1$-[5-(β-D-Ribofuranosyl)-3-cyanopyridine-5'-yl]$P^2$-[2'-deoxyadenosine-5"-yl]methylenediphosphonate, $P^1$-[6-(β-D-Ribofuranosyl)-2-cyanopyridine-5'-yl]-$P^2$-[2'-deoxyadenosine-5"-yl]methylenediphosphonate, $P^1$-[2-(β-D-Ribofuranosyl)-4-cyanopyridine-5'-yl]-$P^2$-[2'-deoxyadenosine-5"-yl]methylenediphosphonate, $P^1$-[5-(β-D-Ribofuranosyl)nicotinamide-5'-yl]-$P^2$-[2'-deoxy-2'-fluoroadenosine-5"-yl]methylenediphosphonate, $P^1$-[6-(β-D-Ribofuranosyl)picolinamide-5'-yl]-$P^2$-[2'-deoxy-2'-fluoroadenosine-5"-yl]methylenediphosphonate, $P^1$-[2-(β-D-Ribofuranosyl)isonicotinamide-5'-yl]-$P^2$-[2'-deoxy-2'-fluoroadenosine-5"-yl]methylenediphosphonate, $P^1$-[5-(β-D-Ribofuranosyl)-3-cyanopyridine-5'-yl]-$P^2$-[2'-deoxy-2'-fluoroadenosine-5"-yl]methylenediphosphonate, $P^1$-[6-(β-D-Ribofuranosyl)-2-cyanopyridine-5'-yl]-$P^2$-[2'-deoxy-2'-fluoroadenosine-5"-yl]methyldiphosphonate, $P^1$-[2-(β-D-Ribofuranosyl)-4-cyanopyridine-5'-yl]-$P^2$-[2'-deoxy-2'-fluoroadenosine-5"-yl]methylenediphosphonate, $P^1$-[5-(β-D-Ribofuranosyl)nicotinamide-5'-yl]-$P^2$-[3'-deoxy-3'-fluoroadenosine-5"-yl]methylenediphosphonate, $P^1$-[6-(β-D-Ribofuranosyl)picolinamide-5'-yl]-$P^2$-[3'-deoxy-3'-fluoroadenosine-5"-yl]methylenediphosphonate, $P^1$-[2-(β-D-Ribofuranosyl)isonicotinamide-5'-yl]-$P^2$-[3'-deoxy-3'-fluoroadenosine-5"-yl]methylenediphosphonate, $P^1$-[5-(β-D-Ribofuranosyl)-3-cyanopyridine-5'-yl]-$P^2$-[3'-deoxy-3'-fluoroadenosine-5"-yl]methylenediphosphonate, $P^1$-[6-(β-D-Ribofuranosyl)-2-cyanopyridine-5'-yl]-$P^2$-[3'-deoxy-3'-fluoroadenosine-5"-yl]methylenediphosphonate, $P^1$-[2-(β-D-Ribofuranosyl)-4-cyanopyridine-5'-yl]-$P^2$-[3'-deoxy-3'-fluoroadenosine-5"-yl]methylenediphosphonate, $P^1$-[5-(β-D-Ribofuranosyl)nicotinamide-5'-yl]-$P^2$-[9-(2'-deoxy-2'-fluoro-β-D-arabinofuranosyl)adenine-5"-yl]methylenediphosphonate, $P^1$-[6-(β-D-Ribofuranosyl)picolinamide-5'-yl]-$P^2$-[9-(2'-deoxy-2'-fluoro-β-D-arabinofuranosyl)adenine-5"-yl]methylenediphosphonate, $P^1$-[2-(β-D-Ribofuranosyl)isonicotinamide-5'-yl]-$P^2$-[9-(2'-deoxy-2'-fluoro-β-D-arabinofuranosyl)adenine-5"-yl]methylenediphosphonate, $P^1$-[5-(β-D-Ribofuranosyl)-3-cyanopyridine-5'-yl]-$P^2$-[9-(2'-deoxy-2'-fluoro-β-D-arabinofuranosyl)adenine-5"-yl]methylenediphosphonate, $P^1$-[6-(β-D-Ribofuranosyl)-2-cyanopyridine-5'-yl]-$P^2$-[9-(2'-deoxy-2'-fluoro-β-D-arabinofuranosyl)adenine-5"-yl]methylenediphosphonate, $P^1$-[2-(β-D-Ribofuranosyl)-4-cyanopyridine-5'-yl]-$P^2$-[9-(2'-deoxy-2'-fluoro-βD-arabinofuranosyl)adenine -5"-yl]methylenediphosphonate, $P^1$-[5-(β-D-Ribofuranosyl)nicotinamide-5'-yl]-$P^2$-[adenosine-5"-yl]difluoromethylenediphosphate, $P^1$-[6-(β-D-Ribofuranosyl)picolinamide-5'-yl]-$P^2$-[adenosine-5"-yl]difluoromethylenediphosphonate, $P^1$-[2-(β-D-Ribofuranosyl)isonicotinamide-5'-yl]-$P^2$-[adenosine-5"-yl]difluoromethylenediphosphonate, $P^1$-[5-(β-D-Ribofuranosyl)-3-cyanopyridine-5'-yl]-$P^2$-[adenosine-5"-yl]difluoromethylenediphosphonate, $P^1$-[6-(β-D-Ribofuranosyl)-2-cyanopyridine-5'-yl]-$P^2$-[adenosine-5"-yl]difluoromethylenediphosphonate, $P^1$-[2-(β-D-Ribofuranosyl)-4-cyanopyridine-5'-yl]-$P^2$-[adenosine-5"-yl]difluoromethylenediphosphonate, $P^1$-[5-(β-D-Ribofuranosyl)nicotinamide-5'-yl]-$P^2$-[2'-deoxyadenosine-5"-yl]difluoromethylenediphosphonate, P¹-[6-(β-D-Ribofuranosyl)picolinamide-5'-yl]-P²-[2'-deoxyadenosine-5''-yl]difluoromethylenediphosphonate, P¹-[2-(β-D-Ribofuranosyl)isonicotinamide-5'-yl]-P²-[2'-deoxyadenosine-5''-yl]-difluoromethylenediphosphonate, P¹-[5-(β-D-Ribofuranosyl)-3-cyanopyridine-5'-yl]P²-[2'-deoxyadenosine-5''-yl]difluoromethylenediphosphonate, P¹-[6-(β-D-Ribofuranosyl)-2-cyanopyridine-5'-yl]-P²-2-deoxyadenosine-5''-yl]difluoromethylenediphosphonate, P¹-[2-(β-D-Ribofuranosyl)-4-cyanopyridine-5'-yl]-P²-[2'-deoxyadenosine-5''-yl]difluoromethylenediphosphonate, P¹-[5-(β-D-Ribofuranosyl)nicotinamide-5'-yl]-P²-[2'-deoxy-2'-fluoroadenosine-5''-yl]difluoromethylenediphosphonate, P¹-[6-(β-D-Ribofuranosyl)picolinamide-5'-yl]-P²-[2'-deoxy-2'-fluoroadenosine-5''-yl]difluoromethylenediphosphonate, P¹-[2-(β-D-Ribofuranosyl)isonicotinamide-5'-yl]P²-[2'-deoxy-2'-fluoroadenosine-5''-yl]difluoromethylenediphosphonate, P¹-[5-(β-D-Ribofuranosyl)-3-cyanopyridine-5'-yl]-P²-[2'-deoxy-2'-fluoroadenosine-5''-yl]difluoromethylenediphosphonate, P¹-[6-(β-D-Ribofuranosyl)-2-cyanopyridine-5'-yl]-P²-[2'-deoxy-2'-fluoroadenosine-5''-yl]difluoromethylenediphosphonate, P¹-[2-(β-D-Ribofuranosyl)-4-cyanopyridine-5'-yl]-P²-[2'-deoxy-2'-fluoroadenosine-5''-yl]difluoromethylenediphosphonate, P¹-[5-(β-D-Ribofuranosyl)nicotinamide-5'-yl]-P²-[3'-deoxy-3'-fluoroadenosine-5''-yl]difluoromethylenediphosphonate, P¹-[6-(β-D-Ribofuranosyl)picolinamide-5'-yl]-P²-[3'-deoxy-3'-fluoroadenosine-5''-yl]difluoromethylenediphosphonate, P¹-(2-β-D-Ribofuranosyl)isonicotinamide-5'-yl-P²-3'-deoxy-3'-fluoroadenosine-5''-yl]difluoromethylenediphosphonate, P¹-[5-(β-D-Ribofuranosyl)-3-cyanopyridine-5'-yl]-P²-[3'-deoxy-3'-fluoroadenosine-5''-yl]difluoromethylenediphosphonate, P¹-[6-(β-D-Ribofuranosyl)-2-cyanopyridine-5'-yl]-P²-[3'-deoxy-3'-fluoroadenosine-5''-yl]difluoromethylenediphosphonate, P¹-[2-(β-D-Ribofuranosyl)-4-cyanopyridine-5'-yl]-P²-[3'-deoxy-3'-fluoroadenosine-5''-yl]-difluoromethylenediphosphonate, P¹-[5-(β-D-Ribofuranosyl)nicotinamide-5'-yl]-P²-[9-(2'-deoxy-2'-fluoro-β-D-arabino-furanosyl)]adenine-5''-yl]-difluoromethylenediphosphonate, P¹-[6-(β-D-Ribofuranosyl)picolinamide-5'-yl]-P²-[9-(2'-deoxy-2'-fluoro-β-D-arabino-furanosyl)]adenine-5''-yl]-difluoromethylenediphosphonate, P¹-[2-(β-D-Ribofuranosyl)isonicotinamide-5'-yl]-P²-[9-(2'-deoxy-2'-fluoro-β-D-arabino-furanosyl)adenine-5''-yl]-difluoromethylenediphosphonate, P¹-[5-(β-D-Ribofuranosyl)-3-cyanopyridine-5'-yl]-P²-[9-(2'-deoxy-2'-fluoro-βD-arabino-furanosyl)adenine-5''-yl]-difluoromethylenediphosphonate, P¹-[6-(β-D-Ribofuranosyl)-2-cyanopyridine-5'-yl]-P²-[9-(2'-deoxy-2'-fluoro-βD-arabino-furanosyl)adenine-5''-yl]-difluoromethylenediphosphonate, and P¹-[2-(β-D-Ribofuranosyl)-4-cyanopyridine-5'-yl]-P²-[9-(2'-deoxy-2'-fluoro-βD-arabino-furanosyl)adenine-5''-yl]-difluoromethylenediphosphonate.

This invention also provides a compound having the structure:

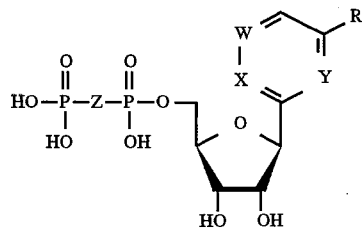

wherein Z is $CH_2$ or $CF_2$; R is chlorine, bromine, iodine, carbonitrile, carboxylic ester, or carboxamide; and one of W, X and Y is N or $N^+R'$, wherein R' is methyl or ethyl, and all others are CH.

Compounds having the above-identified structure, although not limited to the following compounds, may be selected from the group consisting of:

(5-β-D-Ribofuranosylnicotiamide-5'-yl)methylenediphosphonate (6-β-D-Ribofuranosylpicolinamide-5'-yl)methylenediphosphonate, (2-β-D-Ribofuranosylisonicotinamide-5'-yl)methylenediphosphonate, (5-β-D-Ribofuranosyl-3-cyanopyridine-5'-yl)methylenediphosphonate, (6-β-D-Ribofuranosyl-2-cyanopyridine-5'-yl)methylenediphosphonate, (2-(β-D-Ribofuranosyl-4-cyanopyridine-5'-yl)methylenediphosphonate, (5-β-D-Ribofuranosylnicotinamide-5'-yl)difluoromethylene-diphosphonate, (6-β-D-Ribofuranosylpicolinamide-5'-yl)difluoromethylene-diphosphonate, (2-β-D-Ribofuranosylisonicotinamide-5'-yl)difluoromethylene-diphosphonate, (5-β-D-Ribofuranosyl-3-cyanopyridine-5'-yl)difluoromethylene-diphosphonate, (6-β-D-Ribofuranosyl-2-cyanopyridine-5'-yl)difluoromethylene-diphosphonate, and (2-(β-D-Ribofuranosyl-4-cyanopyridine-5'-yl)difluoromethylene-diphosphonate.

This invention also provides a compound having the structure:

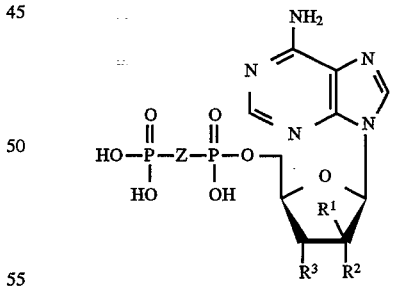

wherein Z is $CH_2$ or $CF_2$; and $R^1$, $R^2$, and $R^3$ are same or different, and are hydrogen, hydroxyl, or fluorine.

Compounds having the above-identified structure, although not limited to the following compounds, may be selected from the group consisting of:

(Adenosin-5'-yl)methylenediphosphonate, (2'-deoxyadenosin-5'-yl)methylene-diphosphonate, (2'-deoxy-2'-fluoroadenosin-5'-yl)methylene-diphosphonate, (3'-deoxy-3'-fluoroadenosin-5'-yl)methylene-diphosphonate,

[9-(2'-deoxy-2'-fluoro-β-D-arabinofuranosyl)adenine-5'-yl] methylenediphosphonate,
(Adenosin-5'-yl)difluoromethylenediphosphonate,
(2'-deoxyadenosin-5'-yl)difluoromethylene-diphosphonate,
(2'-deoxy-2'-fluoroadenosin-5'-yl)difluoromethylene-diphosphonate,
(3'-deoxy-3'-fluoroadenosin-5'-yl)difluoromethylene-diphosphonate, and
[9-(2'-deoxy-2'-fluoro-β-D-arabinofuranosyl)adenine-5'-yl] difluoromethylenediphosphonate.

This invention further provides a method of treating a mammal having a NAD-dependent enzyme associated disorder which comprises administering to the mammal a pharmaceutically effective amount of a compound having the structure:

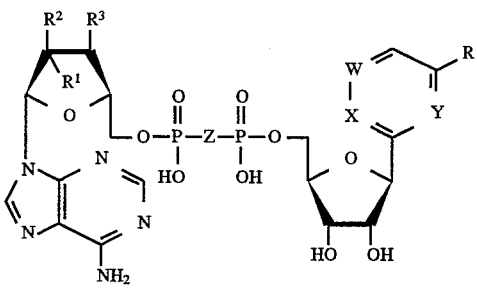

wherein $R^1$, $R^2$, and $R^3$ are same or different, and are hydrogen, hydroxyl, or fluorine; Z is O, $CH_2$ or $CF_2$; R is chlorine, bromine, iodine, carbonitrile, carboxylic ester, or carboxamide; and one of W, X and Y is N or $N^+R'$, wherein R' is methyl or ethyl, and all others are CH;
effective to inhibit the NAD-dependent enzyme, thereby treating the disorder.

For the purpose of this invention, the term "NAD-dependent enzyme" means an enzyme which requires the presence of the co-enzyme NAD in order to assist the enzymatic reaction. Examples of enzymes which are dependent on NAD are known to those skilled in the art and include, but are not limited to, malate dehydrogenase, lactate dehydrogenase, alcohol dehydrogenase, inosine, monophosphat dehydrogenase, glutamate dehydrogenase, isocitrate dehydrogenase, 6-phosphogluconate dehydrogenase, aldehyde dehydrogenase, dihydrosteroid dehydrogenase and dihydrofolate reductase.

For the purposes of this invention, the term "NAD-dependent enzyme associated disorder" is any disorder which arises or is aggravated due to the enzymatic action of an NAD-dependent enzyme. Examples of such disorders are readily determinable by those skilled in the art.

In a preferred embodiment of this invention the NAD-dependent enzyme is alcohol dehydrogenase. In a second preferred embodiment of this invention the NAD-dependent enzyme is inosine monophosphate dehydrogenase.

Examples of disorders associated with the enzymatic action of alcohol dehydrogenase include, but are not limited to, acute alcohol poisoning from the ingestion of such substances as ethanol, methanol or isopropyl alcohol, ethylene glycol intoxication, ethanol-induced hypoglycemia and lactacidemia.

Examples of disorders associated with the enzymatic action of inosine monophosphate dehydrogenase include, but are not limited to disorders characterized by the proliferation of malignant cells. Examples of disorders which are associated with the proliferation of malignant cells to which the compounds of the subject invention would be effective are readily determinable by those skilled in the art and include, but are not limited to, cancers of the breast, colon, stomach, pancreas, ovary, head and neck, and urinary bladder, leukemias such as acute lymphocytic, acute granulocytic and chronic granulocytic leukemias, hairy cell leukemia, chronic lymphocytic leukemia, and other malignant disorders such as mycosis fungoides.

This invention also provides a pharmaceutical composition which comprises any of the above-identified compounds and a pharmaceutically acceptable carrier. In the preferred embodiment of this invention, the compounds are administered to the mammal as a pharmaceutical composition.

As used herein, the term "pharmaceutically acceptable carrier" encompasses any of the standard pharmaceutical carriers such as an organic or inorganic inert carrier material suitable for enteral or parenteral administration which include, but are not limited to, water, gelatin, gum arabic, lactose, starches, magnesium stearate, talc, vegetable oils, polyalkylene glycols, petroleum gelly, etc. The pharmacological preparations can be made up in solid form such as tablets, dragees, suppositories or capsules, or in liquid form such as solutions, suspensions, or emulsions. The preparations may be sterilized and/or contain adjuvants such as preserving, stabilizing, wetting or emulsifying agents, salts for varying the osmotic pressure, or buffers. Such preparations may also contain other therapeutic agents.

For the purposes of this invention, the term "pharmaceutically effective amount" of the compound means any amount of the compound which, when incorporated in the pharmaceutical composition, will be effective to inhibit the enzymatic action of an NAD-dependent enzyme and, thereby, treat an NAD-dependent enzyme associated disorder but less than an amount which would be toxic to the mammal. In the practice of this invention the amount of the compound incorporated in the pharmaceutical composition may vary widely. Factors considered when determining the precise amount are well known to those skilled in the art. Examples of such factors include, but are not limited to, the subject being treated, the specific pharmaceutical carrier and route of administration being employed and the frequency with which the composition is to be administered. In a preferred embodiment of this invention, the pharmaceutically effective amount of the compound is in the range of 10 picomolar to 10 milimolar. In a particularly preferred embodiment the pharmaceutically effective amount is in the range of 10 micromolar.

In the practice of this invention, the administration of the composition may be effected by any of the well known methods including, but not limited to, oral, intravenous, intraperitoneal, intramuscular or subcutaneous or topical administration.

The compounds of this invention are prepared according to the following methods.

In the first method, the nucleosides are converted to their corresponding 5'-monophosphates and then coupled together to form the dinucleotides of this invention as follows:

(a) reacting a compound having the structure:

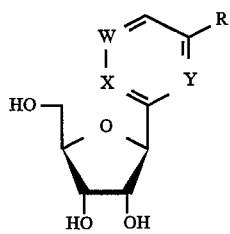

Formula II wherein R is chlorine, bromine, iodine, carbonitrile, carboxylic ester, or carboxamide; and one of W, X and Y is N or N⁺R', wherein R' is methyl or ethyl, and all others are CH;
with phosphorous oxychloride in triethylphosphate under suitable conditions to form the nucleoside 5'-monophosphate derivative of the compound;

(b) reacting a compound having the structure:

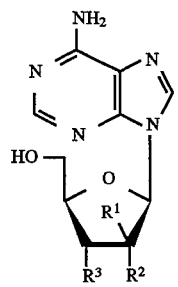

Formula III wherein $R^1$, $R^2$, and $R^3$ are same or different, and are hydrogen, hydroxyl, or fluorine;
with phosphorous oxychloride in triethylphosphate under suitable conditions to form the nucleoside 5'-monophosphate derivative of the compound; and (c) reacting the 5'-monophosphate derivative formed in step (a) or (b) with carbonyldiimidazole or dicyclohexyl carbodiimide under suitable conditions to activate the 5'-monophosphate derivative and then contacting the activated compound with an unactivated compound of step (b) or (a), respectively, to form a compound having the structure:

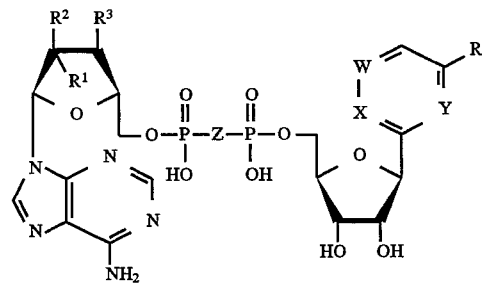

wherein $R^1$, $R^2$, and $R^3$ are same or different, and are hydrogen, hydroxyl, or fluorine; Z is O; R is chlorine, bromine, iodine, carbonitrile, carboxylic ester, or carboxamide; and one of W, X and Y is N or N⁺R', wherein R' is methyl or ethyl, and all others are CH;

This method proceeds along the lines of known methods for the formation of the 5'-monophosphate derivatives of nucleosides; Yoshikawa et al., *Tetrahedron Letters*, 1967, 19, 5065-5068.

The dinucleotides of this invention, wherein Z is $CH_2$ or $CF_2$, can also be prepared by first forming the 5'-methylene-diphosphonate or 5'-difluoromethylene-diphosphonate derivative nucleosides of this invention and then coupling the derivatives to the corresponding nucleosides bearing the 5'-hydroxy group. The method proceeds as follows:

(a) reacting a compound having the structure:

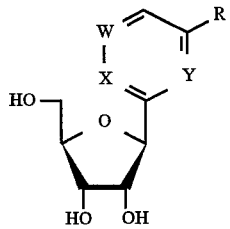

wherein R is chlorine, bromine, iodine, carbonitrile, carboxylic ester, or carboxamide; and one of W, X and Y is N or N⁺R', wherein R' is methyl or ethyl, and all others are CH;
with the precursor of a suitable protecting group under suitable conditions to form the 2'3'-O-protected nucleoside; and (b) reacting the compound formed in step (a) with methylenediphosphonate tetrachloride in triethylphosphate under suitable conditions to form the 5'-methylenediphosphonate derivative, which, after reacting under suitable conditions to selectively remove the 2',3'-O-protecting groups, has the structure:

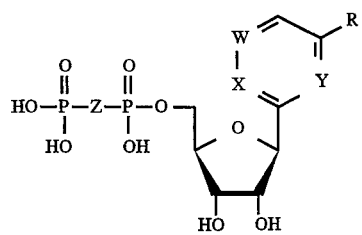

wherein Z is $CH_2$; R is chlorine, bromine, iodine, carbonitrile, carboxylic ester, or carboxamide; and one of W, X and Y is N or N⁺R', wherein R' is methyl or ethyl, and all others are CH.

The dinucleotides of the invention are then prepared by reacting the 5'-methylenediphosphonate derivative formed above with the nucleoside having the structure:

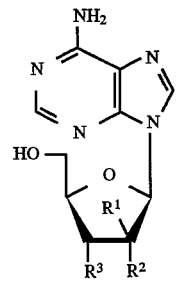

wherein $R^1$, $R^2$, and $R^3$ are same or different, and are hydrogen, hydroxyl, or fluorine;
under suitable conditions to allow for the coupling of the nucleosides to form the compound having the structure:

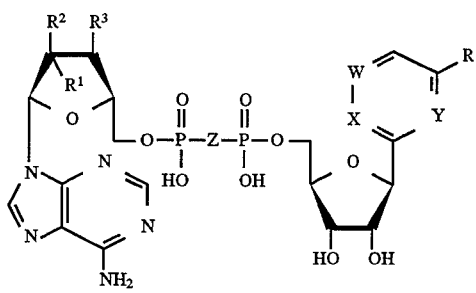

wherein Z is CH$_2$; R is chlorine, bromine, iodine, carbonitrile, carboxylic ester, or carboxamide; R$^1$, R$^2$, and R$^3$ are same or different, and are hydrogen, hydroxyl, or fluorine; and one of W, X and Y is N or N$^+$R', wherein R' is methyl or ethyl, and all others are CH.

The 5'-methylenediphosphonate derivative of the compound having the structure:

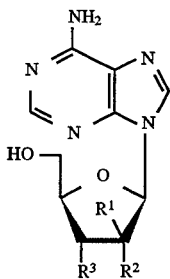

wherein R$^1$, R$^2$, and R$^3$ are same or different, and are hydrogen, hydroxyl, or fluorine;

is formed by the same method as above, wherein step (a) and the deprotection in step (b) are necessary only if any of R$^1$, R$^2$, and R$^3$ are hydroxyl groups.

The dinucleotides of the invention are then prepared by reacting the 5'-methylenediphosphonate derivative formed above with the nucleoside having the structure:

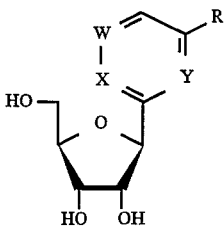

wherein R is chlorine, bromine, iodine, carbonitrile, carboxylic ester, or carboxamide; and one of W, X and Y is N or N$^+$R', wherein R' is methyl or ethyl, and all others are CH;

under suitable conditions to allow for the coupling of the nucleosides to form the compound having the structure:

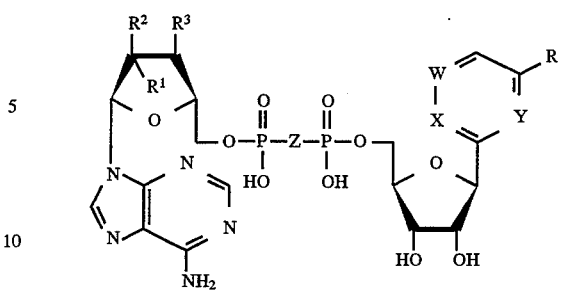

wherein Z is CH$_2$; R is chlorine, bromine, iodine, carbonitrile, carboxylic ester, or carboxamide; R$^1$, R$^2$, and R$^3$ are same or different, and are hydrogen, hydroxyl, or fluorine; and one of W, X and Y is N or N$^+$R', wherein R' is methyl or ethyl, and all others are CH.

In this method the reaction of step (a) comprises the selective protection of the vicinal cis hydroxy groups on the nucleoside to leave the 5'hydroxyl group as the remaining reactive site. For the purpose of this invention, a "precursor of a suitable protecting group" will comprise any compound that can be reacted with the compound of step (a) to allow for selective replacement of the vicinal hydroxyl cis hydroxy group with the corresponding O-protecting group. Examples of these are well known to those skilled in the art and include, but are not limited to, such compounds as isopropylidene and ethyl orthoformate. In this step the molar ratio of the reactants is in the range of 1:10 to 1:100 and the reaction is carried out at a temperature range of 0° C. to 50° C. for a period of 5 minutes to 2 days.

The reaction of step (b) comprises the formation of the 5'-methylenediphosphonate derivatives by reacting the compound formed in step (a) with methylenediphosphonate tetrachloride in triethylphosphate. In this step the molar ratio of the reactants is in the range of 2:1 to 1:10 and the reaction is carried out at a temperature range of –20° C. to 50° C. for a period of 5 minutes to 10 hours. Step (b) also comprises the selective removal of any protecting groups to form the 2',3'-hydroxy group substituents. The conditions of this step comprise acidic hydrolysis using Dowex 50 (H$^+$), organic acid such as acetic acid, trifluoroacetic acid an the like, or inorganic acid such as hydrochloric acid, sulfuric acid and the like.

The coupling of the nucleosides is then carried out under reaction conditions of . . .

This invention also provides another method of making the dinucleotides of this invention wherein Z is CH2 or CF2 which proceeds as follows:

a) reacting a compound having the structure:

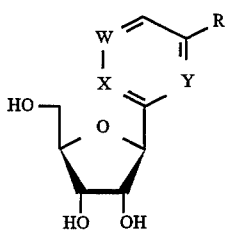

OR

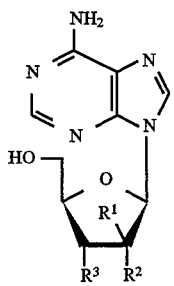

wherein R, R¹, R², R³, W, X and Y are the same as defined previously;

with the precursor of a suitable protecting group to under suitable conditions to selectively protect the 2' and 3' hydroxyl groups on the compounds;

b) reacting the compounds formed in step (a) with tosyl chloride under tosylating conditions to form the compounds having the structure:

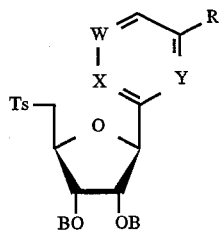

OR

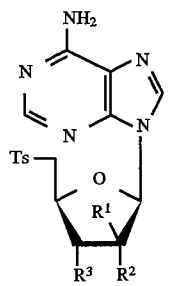

wherein Ts is tosyl and R, W, X and Y are the same as defined previously B is a protecting group and R¹, R², and R³ are hydrogen, fluorine or an O-protecting group;

c) reacting the compound formed in step (b) with tris (tetra-n-butylammonium)methylene diphosphonate or tris(tetra-n-butylammonium)difluoromethylene diphosphonate in dimethylsulfoxide to form compounds having the structure:

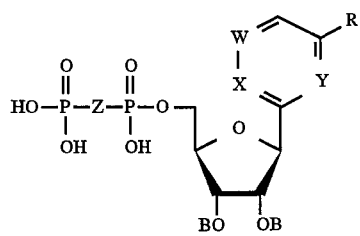

OR

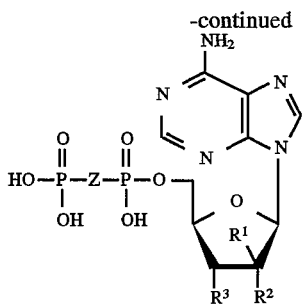

wherein Z is $CH_2$ or $CF_2$ and B, R, R¹, R², R³, W, X and Y are the same as defined previously;

d) reacting the compound formed in step (c) with a compound having the structure:

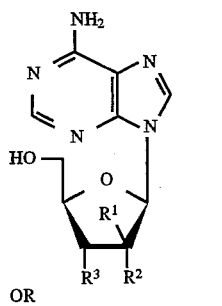

OR

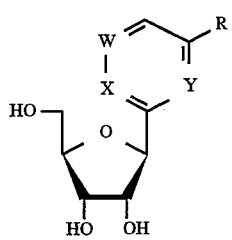

respectively, wherein R, W, X and Y are the same as defined previously and R¹, R², R³ are hydrogen, hydroxy or fluorine;

under suitable conditions to form a compound having the structure:

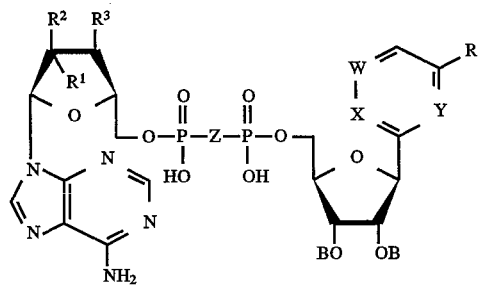

wherein Z is $CH_2$ or $CF_2$ and R, W, X and Y are the same as defined previously and R¹, R², R³ are hydrogen, hydroxy, fluorine or O-protecting groups and B is H or a protecting group; and e) reacting the compound formed in step (d) under suitable conditions to selectively remove the protecting groups to form the compound having the structure:

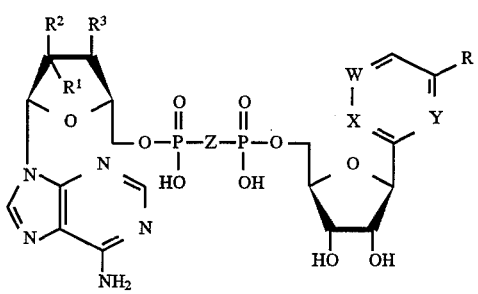

wherein Z is $CH_2$ or $CF_2$ and R, W, X and Y are the same as defined previously and $R^1$, $R^2$, $R^3$ are hydrogen, hydroxy or fluorine.

In this embodiment, the reaction of step (a) comprises the selective protection of the vicinal cis hydroxy groups on the nucleoside to leave the 5'hydroxyl group as the remaining reactive site. For the purpose of this invention, a "precursor of a suitable protecting group" will comprise any compound that can be reacted with the compound of step (a) to allow for selective replacement of the vicinal hydroxyl cis hydroxy group with the corresponding O-protecting group. Examples of these are well known to those skilled in the art and include, but are not limited to, such compounds as isopropylidene and ethyl orthoformate. In this step the molar ratio of the reactants is in the range of 1:1 to 1:100 and the reaction is carried out at a temperature range of 0° C. to 50° C. for a period of 5 minutes to 2 days.

The reaction of step (b) comprises the replacement of the 5'hydroxy group with a tosyl leaving group by reacting the compound formed in step (a) with tosyl chloride. In this step the molar ratio of the reactants is in the range of 1:1 to 1:10 and the reaction is carried out at a temperature range of −10° C. to 50° C. for a period of 5 minutes to 2 days.

The reaction of step (c) comprises the formation of the methylene- or difluoromethylene-diphosphonate derivative of the compound formed in step (b) by reacting the compound formed in step (b) with tris(tetra-n-butylammonium) methylene diphosphonate or tris(tetra-n-butylammonium) difluoromethylene diphosphonate, respectively, in dimethylsulfoxide. In this step the molar ratio of the reactants is in the range of 1:1 to 1:100 and the reaction is carried out at a temperature range of 0° C. to 50° C. for a period of 5 minutes to 10 days.

The reaction of step (d) comprises the coupling of the compound formed in step (c) with the corresponding nucleoside to form the dinucleotide complexes of this invention after deprotection in step (e). In step (d) the molar ratio of the reactants is in the range of 1:1 to 1:20 and the reaction is carried out at a temperature range of 0° C. to 50° C. for a period of 5 minutes to 10 days. In step (e), the deprotection of the compounds formed in step (d) is carried out at a temperature range of −20° C. to 50° C. for a period of 5 minutes to 1 day.

The subject invention provides a compound having the structure:

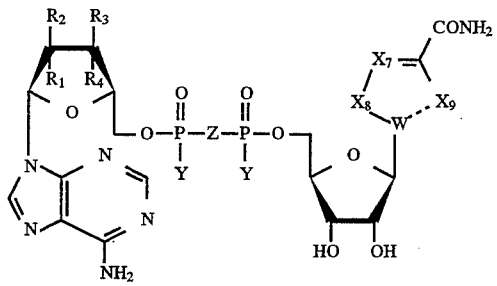

wherein each $R_1$, $R_2$, $R_3$, and $R_4$ is independently fluorine, OH or H; Z is O, $CH_2$ or $CF_2$; each Y is independently OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH.

The subject invention also provides a compound having the structure:

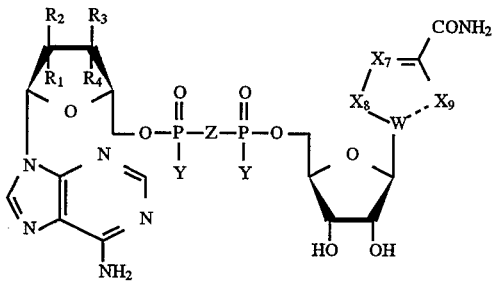

wherein one of $R_1$, $R_2$, $R_3$, and $R_4$ is fluorine, one is OH and the remainder are H; Z is O, $CH_2$ or $CF_2$; each Y is independently OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH.

In a preferred embodiment, the compound defined above has the structure:

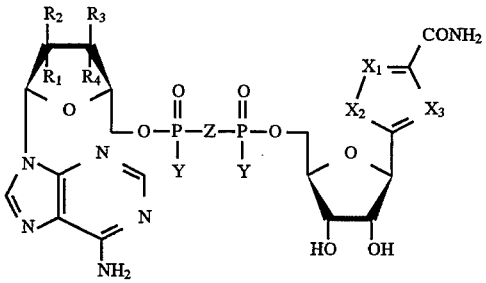

wherein one of $R_1$, $R_2$, $R_3$, and $R_4$ is fluorine, one is OH and the remainder are H; Z is O, $CH_2$ or $CF_2$; each Y is independently OH or F; $X_1$ is N or CH, $X_2$ is NH, S or Se; and $X_3$ is N or CH.

In another preferred embodiment the compound defined above has the structure:

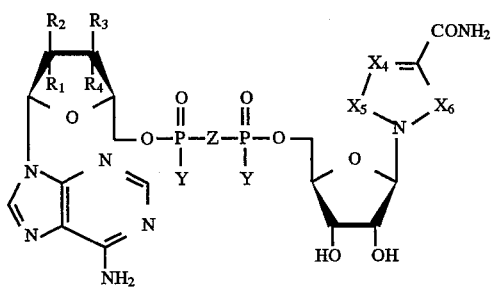

wherein one of $R_1$, $R_2$, $R_3$, and $R_4$ is fluorine, one is OH and the remainder are H; Z is O, $CH_2$ or $CF_2$; each Y is independently OH or F; $X_4$ is N or CH, $X_5$ is NH, S or Se; and $X_6$ is NH, CH, S or Se.

The subject invention also provides a compound having the structure:

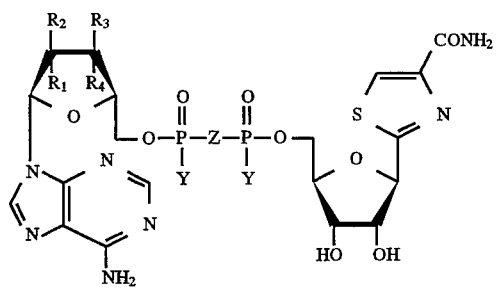

wherein one of $R_1$, $R_2$, $R_3$, and $R_4$ is fluorine, one is OH and the remainder are H; each Y is independently F or OH, and Z is O, $CH_2$ or $CF_2$.

In a preferred embodiment, the compound defined above has the structure:

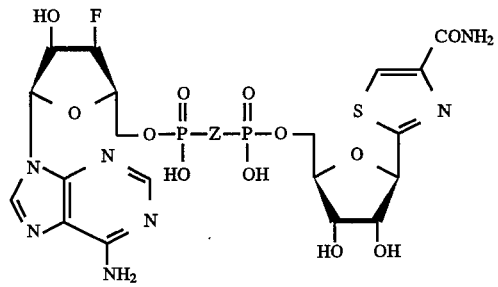

wherein each Y is independently F or OH, and Z is O, $CH_2$ or $CF_2$.

In another preferred embodiment, the compound defined above has the structure:

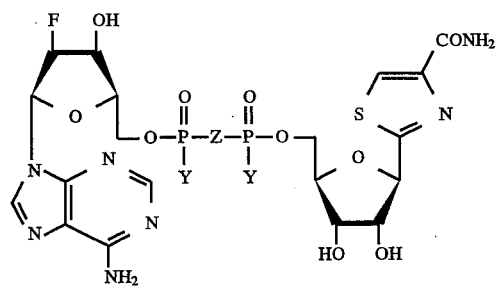

wherein each Y is independently F or OH, and Z is O, $CH_2$ or $CF_2$.

In an additional preferred embodiment the compound defined above has the structure:

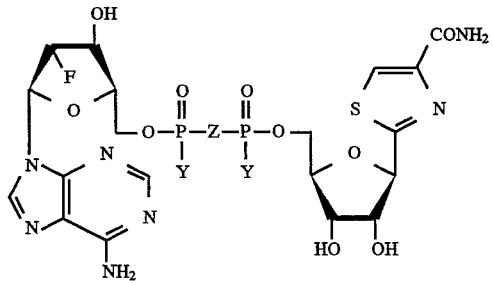

wherein each Y is independently F or OH, and Z is O, $CH_2$ or $CF_2$.

The subject invention also provides a pharmaceutical composition which comprises any of the compounds defined above and a pharmaceutically acceptable carrier.

The subject invention further provides a method of treating a mammal having an inosine monophosphate dehydrogenase associated disorder which comprises administering to the mammal a therapeutically effective amount of a compound having the structure:

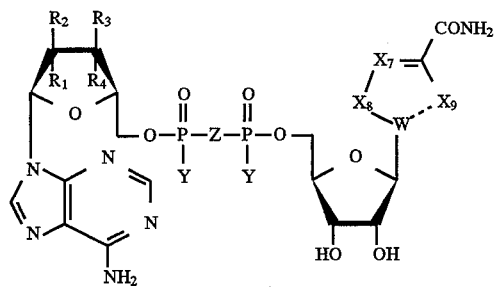

wherein one of $R_1$, $R_2$, $R_3$, and $R_4$ is fluorine, one is OH and the remainder are H; Z is O, $CH_2$ or $CF_2$; each Y is independently OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH;
effective to inhibit inosine monophosphate dehydrogenase, thereby treating the disorder.

The subject invention also provides a method of treating a mammal having an inosine monophosphate dehydrogenase associated disorder which comprises administering to the mammal a therapeutically effective amount of a compound having the structure:

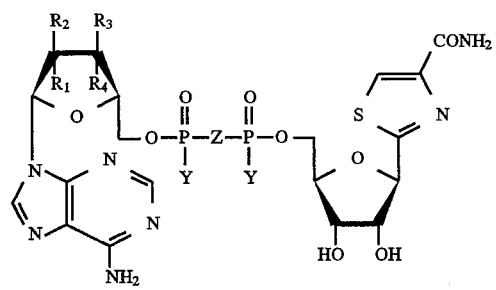

wherein one of $R_1$, $R_2$, $R_3$, and $R_4$ is fluorine, one is OH and the remainder are H; each Y is independently F or OH, and Z is O, $CH_2$ or $CF_2$;

effective to inhibit inosine monophosphate dehydrogenase thereby treating the disorder.

Examples of disorders associated with the enzymatic action of inosine monophosphate dehydrogenase include, but are not limited to disorders characterized by the proliferation of malignant cells. Examples of disorders which are associated with the proliferation of malignant cells to which the compounds of the subject invention would be effective are readily determinable by those skilled in the art and include, but are not limited to, cancers of the breast, colon, stomach, pancreas, ovary, head and neck, and urinary bladder, leukemias such as acute lymphocytic, acute granulocytic and chronic granulocytic leukemias, hairy cell leukemia, chronic lymphocytic leukemia, and other malignant disorders such as mycosis fungoides.

This invention also provides a pharmaceutical composition which comprises any of the above-identified compounds and a pharmaceutically acceptable carrier. In the preferred embodiment of this invention, the compounds are administered to the mammal as a pharmaceutical composition.

As used herein, a "mammal" is any member of the higher vertibrate animals comprising the class Mammalia, the highest class of the subphylum Vertebrata. In a preferred embodiment of the subject invention the mammal is human.

As used herein, the term "pharmaceutically acceptable carrier" encompasses any of the standard pharmaceutical carriers such as an organic or inorganic inert carrier material suitable for enteral or parenteral administration which include, but are not limited to, water, gelatin, gum arabic, lactose, starches, magnesium stearate, talc, vegetable oils, polyalkylene glycols, petroleum gelly, etc. The pharmacological preparations can be made up in solid form such as tablets, dragees, suppositories or capsules, or in liquid form such as solutions, suspensions, or emulsions. The preparations may be sterilized and/or contain adjuvants such as preserving, stabilizing, wetting or emulsifying agents, salts for varying the osmotic pressure, or buffers. Such preparations may also contain other therapeutic agents.

For the purposes of this invention, the term "therapeutically effective amount" of the compound means any amount of the compound which, when incorporated in the pharmaceutical composition, will be effective to inhibit the enzymatic action of inosine monophoshate dehydrogenase and, thereby, treat an inosine monophosphate enzyme associated disorder but less than an amount which would be toxic to the mammal. In the practice of this invention the amount of the compound incorporated in the pharmaceutical composition may vary widely. Factors considered when determining the precise amount are well known to those skilled in the art. Examples of such factors include, but are not limited to, the subject being treated, the specific pharmaceutical carrier and route of administration being employed and the frequency with which the composition is to be administered. In a preferred embodiment of this invention, the therapeutically effective amount of the compound is in the range of 10 picomolar to 10 milimolar. In a particularly preferred embodiment the therapeutically effective amount is in the range of 10 micromolar.

In the practice of this invention, the composition may be administered by any of the well known methods including, but not limited to, oral, intravenous, intraperitoneal, intramuscular, subcutaneous or topical administration. This invention is further illustrated in the Experimental Details section which follow. The Experimental Details section and Examples contained therein are set forth to aid in an understanding of the invention. This section is not intended to, and should not be interpreted to, limit in any way the invention set forth in the claims which follow thereafter.

Experimental Details

Preparation of the compounds

EXAMPLE 1

5-($\beta$-D-Ribofuranosyl)nicotinamide-(5'-5")-adenosine pyrophosphate.

To a suspension of 5-($\beta$-D-ribofuranosyl)nicotinamide (100 mg, 0.4 mmol) in triethylphosphate (0.4 mL) is added phosphoryl chloride (72 mg, 0.48 mmol) at 0° C., and the mixture is stirred at room temperature for 4 hours. The reaction is quenched by addition of water (5 mL), and the mixture is neutralized with concentrated ammonia. The crude product is purified on a column of DEAE Sephadex A-25 (bicarbonate form) with 0.1M tetraethylammonium bicarbonate and then on a Dowex 50W-X8 ($H^+$) column to give the desired nucleoside 5'-monophosphate (76 mg). This compound is dried by coevaporation with pyridine (3×5 mL) and dimethylformamide (3×5 mL), and the residue is dissolved in dimethylformamide (0.7 mL). Carbonyldiimidazole (186 mg, 1.15 mmol) is added, and the progress of reaction was followed by thin layer chromatography (iPrOH-conc.$NH_4OH$—$H_2O$, 6;3;1, v/v/v). The excess of carbonyldiimidazole is hydrolyzed by addition of methanol (76 µL), and a solution of adenosine 5'-monophosphate (126 mg, 0.35 mmol) in dimethylformamide (4.4 mL) containing tributylamine (80 uL, 0.35 mmol) is added. The reaction mixture is stirred for 3 days. Water (10 mL) is added, and the mixture is concentrated in vacuo. The gummy residue is dissolved in water (40 mL) containing sodium acetate (60 mg) and extracted with chloroform (2×40 mL) and diethyl ether (2×40 mL). The aqueous layer is treated with triethylamine (60 mL, pH=10) and then lyophilized. The residue is purified on preparative cellulose plate using iPrOH-conc.$NH_4OH$—$H_2O$ (6:3:1), and then by a column of Dowex 50W-X8 ($H^+$)to give the desired pyrophosphate (90 mg, 60%) as a white powder. $^1N$ NMR ($D_2O$) $\delta$ 4.11–4.41 (m, 8H, H3', H3", H4',H4", H5',H5', H5", H5"), 4.54 ($\psi$t, 1H, H2'), 4.76 ($\psi$t, 1H, H2"), 5.06 (d, 1H, H1', $J_{1',2'}$=7.2 Hz), 6.14 (d, 1H, H1", $J_{1",2"}$=5.2 Hz), 8.43, 8.62 (two 1H singlets, H2, H8), 8.95–9.19 (m, 5H, H2, H4, H6, $NH_2$). MS (FAB) m/e 662 (M—H)$^-$; 664 $MH^+$ By following the same procedure, but using the corresponding nucleoside of Formula II instead of nicotinamide riboside, the following dinucleoside pyrophosphates are prepared:

6-($\beta$-D-Ribofuranosyl)picolinamide-(5'-5")-adenosine pyrophosphate, 2-($\beta$-D-Ribofuranosyl)isonicotinamide-(5'-5")-adenosine pyrophosphate, 5-($\beta$-D-Ribofuranosyl)-3-cyanopyridine-(5'-5")-adenosine pyrophosphate, 6-($\beta$-D-Ribofuranosyl)-2-cyanopyridine-(5'-5")-adenosine pyrophosphate, and 2-($\beta$-D-Ribofuranosyl)-4-cyanopyridine-(5'-5")-adenosine pyrophosphate.

EXAMPLE 2

6-($\beta$-D-Ribofuranosyl)picolinamide-(5'-5")-2"-deoxy-2"-fluoroadenosine pyrophosphate (Compound 2).

To a suspension of 6-($\beta$-D-ribofuranosyl)picolinamide (0.195 mmol) in triethylphosphate (0.195 mL) is added phosphoryl chloride (36 mg, 0.24 mmol) at 0° C., the mixture is stirred at room temperature 4 hours, and the diluted with water (5 mL). After addition of concentrated ammonia, the crude product is purified on a DEAE Sephadex A-25 column (bicarbonate form) with 0.1M tetraethylammonium bicarbonate and Dowex 50W-X8 (H⁺ form) to give 5'-monophosphate in 60–70% yield. The compound is then converted into the dinucleotide in reaction with 2'-deoxy-2'-fluoroadenosine 5'-monophosphate as described above. $^1$H NMR (D$_2$O) δ 4.15–4.45 (m, 8H, H2', H3', H5', H5', H4", M5", H5"), 4.61 (ddd, 1H, H3", J$_{2",3"}$=4.4 Hz, J$_{3",4"}$=7.3 Hz, J$_{3",F}$=20.4 Hz), 5.20 (ddd, 1H, H2", J$_{1",2"}$=2.0 Hz, J$_{2",F}$=51.9 Hz), 6.25 (dd, 1H, H1", J$_{1",F}$=16.0 Hz), 7.61 (dd, H5, J$_{3,5}$=1.0 Hz, J$_{4,5}$=7.7 Hz), 7.73 (dd, 1H, H3, J$_{3,4}$=7.7 Hz), 7.84 (t, 1H, H4, J$_{3,4}$=J$_{4,5}$=7.7 Hz), 8.11, 8.27 (two 1H singlets, H2, H8), $^{31}$P NMR (D$_2$O) δ–10.6, δ–10.7; J$_{POP}$= 21.0 Hz. MS (FAB) m/e 662 (M—H)⁻, 664 MH⁺

By following the same procedure, but using the corresponding nucleoside of Formula III instead of adenosine, the following dinucleoside pyrophosphates are prepared:

5-(β-D-Ribofuranosyl)nicotinamide-(5'-5")-2'-deoxyadenosine pyrophosphate,
2-(β-D-Ribofuranosyl)isonicotinamide-(5'-5")-2'-deoxyadenosine pyrophosphate,
5-(β-D-Ribofuranosyl)-3-cyanopyridine-(5'-5")-2'-deoxyadenosine pyrophosphate,
6-(β-D-Ribofuranosyl)-2-cyanopyridine-(5'-5")-2'-deoxyadenosine pyrophosphate,
2-(β-D-Ribofuranosyl)-4-cyanopyridine-(5'-5")-2'-deoxyadenosine pyrophosphate,
5-(β-D-Ribofuranosyl)nicotinamide-(5'-5")-2'-deoxy-2'-fluoroadenosine pyrophoshate,
2-(β-D-Ribofuranosyl)isonicotinamide-(5'-5")-2'-deoxy-2'-fluoroadenosine pyrophosphate,
5-(β-D-Ribofuranosyl)-3-cyanopyridine-(5'-5")-2'-deoxy-2'-fluoroadenosine pyrophosphate,
6-(β-D-Ribofuranosyl)-2-cyanopyridine-(5'-5")-2'-deoxy-2'-fluoroadenosine pyrophosphate,
2-(β-D-Ribofuranosyl)-4-cyanopyridine-(5'-5")-2'-deoxy-2'-fluoroadenosine pyrophosphate,
6-(β-D-Ribofuranosyl)picolinamide-(5'-5")-3'-deoxy-3'-fluoroadenosine pyrophosphate,
2-(β-D-Ribofuranosyl)isonicotinamide-(5'-5")-3'-deoxy-3'-fluoroadenosine pyrophosphate,
5-(β-D-Ribofuranosyl)-3-cyanopyridine-(5'-5")-3'-deoxy-3'-fluoroadenosine pyrophosphate,
6-(β-D-Ribofuranosyl)-2-cyanopyridine-(5'-5")-3'-deoxy-3'-fluoroadenosine pyrophosphate,
2-(β-D-Ribofuranosyl)-4-cyanopyridine-(5'-5")-3'-deoxy-3'-fluoroadenosine pyrophosphate,
6-(β-D-Ribofuranosyl)picolinamide-(5'-5")-9-(2'-deoxy-2'-fluoro-β-D-arabinofuranosyl)adenine pyrophosphate,
2-(β-D-Ribofuranosyl)isonicotinamide-(5'-5")-9-(2'-deoxy-2-fluoro-β-D-arabinofuranosyl)adenine pyrophosphate,
5-(β-D-Ribofuranosyl)-3-cyanopyridine-(5'-5")-9-(2'-deoxy-2'-fluoro-β-D-arabinofuranosyl)adenine pyrophosphate,
6-(β-D-Ribofuranosyl)-2-cyanopyridine-(5'-5")-9-(2'-deoxy-2'-fluoro-β-D-arabinofuranosyl)adenine pyrophosphate, and
2-(β-D-Ribofuranosyl)-4-cyanopyridine-(5'-5")-9-(2'-deoxy-2'fluoro-β-D-arabinofuranosyl)adenine pyrophosphate.

EXAMPLE 3

(5-β-D-Ribofuranosylnicotiamide-5'-y1) methylenediphosphonate.

The 5-β-D-Ribofuranosylnicotiamide (253 mg, 1 mmol) was dissolved in acetone (5 mL), 2,2-dimethoxypropane (1 mL) and p-toluenosulfonic acid (380, 2 mmol) was added and the mixture was stirred at room temperature for 5 h. The mixture was neutralized with NaHCO$_3$, filtered, and concentrated in vacuo. The residue was extracted with chloroform (3×5 mL), the organic solution was washed with water (2×3 mL) and concentrated in vacuo to give 2',3'-O-isopropylidene-5-β-D-ribofuranosylnicotinamide (290, 99%). $^1$H NMR (CDCl$_3$) δ 1.32 (s, 3H, iPr), 1.58 (s, 3H, iPr), 3.72–3.95 (m, 2H, H5', H5"), 4.17–4.21 (m, 1H, H4'), 4.40–4.50 (m, 1H, H3'), 4.71–4.80 (m, 1H, H2'), 4.83 (d, 1H, H1', J$_{1',2'}$=5.3 Hz), 6.90 (brs, 1H, NH$_2$), 7.56 (brs, 1H, NH$_2$), 8.19 (s, 1H, H4), 8.60 (s, 1H, H6), 8.86 (s, 1H, H2). The 2',3'-O-isopropylidene-5-β-D-ribofuranosylnicotinamide (290 mg, 0.99 mmol) was added into solution of methylene diphosphonate tetrachloride (250 mg, 1 mol) in triethylphospate (5 mL). The mixture was stirred at room temperature for 2 h, poured into ice water (10 mL), stirred for 30 min., and then whole mixture was extracted with ethyl acetate (3×10 mL). The pH of the water solution was adjusted to 2 with HCl, the mixture was kept standing for 2 h and concentrated. The residue was purified on preparative HPLC column (Dynamax-300A C18 83 243 C, rate flow 20 mL/min. ) with 0.1M TEAB followed by linear gradient of 0.1 TEAB/ag. acetonitrile (70%) to give (5-β-D-ribofuranosylnicotinamide-5'-yl)methylenediphosphonate (440 mg, 72%) as bis triethylammonium salt. $^1$H NMR (D$_2$O δ 2.12 (t, 2H, CH$_2$, J$_{P,H}$=20 Hz), 4.05–4.40 (m, 4H, H3', H4', H5', H5"), 4.55 (pseudot, 1H, H2'), 4.79 (d, 1H, H1', J$_{1',2'}$=4.9 Hz), 8.40 (s, 1H, H4), 8.72 (s, 1H, H4), 8.91 (s, 1H, H2). $^-$P NMR (D$_2$O) δ 11.5 (d, J$_{P,P}$=9.5 Hz), 22.8 (d).

By following the same procedure, but using the corresponding nucleoside of Formula II instead of nicotinamide riboside, the following methylenediphosphonates are prepared:

(6-β-D-Ribofuranosylpicolinamide-5'-yl) methylenediphosphonate,
(2-β-D-Ribofuranosylisonicotinamide-5'-yl) methylenediphosphonate,
(5-β-D-Ribofuranosyl-3-cyanopyridine-5'-yl) methylenediphosphonate,
(6-β-D-Ribofuranosyl-2-cyanopyridine-5'-yl) methylenediphosphonate, and
(2-(β-D-Ribofuranosyl-4-cyanopyridine-5'-yl) methylenediphosphonate.

EXAMPLE 4

(Adenosin-5'-yl)methylenediphosphonate.

The 2',3'-O-isopropylidene adenosine (307 mg, 1 mmol) was added into solution of methylene diphosphonate tetrachloride (250 mg, 1 mol) in triethylphosphate (5 mL). The mixture was stirred at room temperature for 2 h, poured into ice water (10 mL), stirred for 30 min., and then whole mixture was extracted with ethyl acetate (3×10 mL). The pH of the water solution was adjusted to 2 with HCl, the mixture was kept standing for 2 h and concentrated. The residue was purified on preparative HPLC column (Dynamax-300A C18 83 243 C, rate flow 20 mL/min.)with 0.1M TEAB followed by linear gradient of 0.1 TEAB/ag. acetonitrile (70%) to give (adenosin-5'-yl)methylenediphosphonate (452 mg, 72%) as bis triethylammonium salt. This compound was identical with the corresponding sample prepared by the reaction of 5'-tosyl adenosine with tris(tetra-n-butylammonium) methylenediphosphonate (Example 6).

By following the same procedure, but using the corresponding nucleoside of Formula III instead of adenosine, the following methylenediphosphonates are prepared:
(2'-deoxyadenosin-5'-yl)methylenediphosphonate, (2'-deoxy-2'-fluoroadenosin-5'-yl)methylenediphosphonate,
(3'-deoxy-3'-fluoroadenosin-5'-yl)methylenediphosphonate, and
[9-(2'-deoxy-2'-fluoro-β-D-arabinofuranosyl)adenine-5'-yl] methylenediphosphonate.

EXAMPLE 5

(5-β-D-Ribofuranosylnicotinamide-5'-yl) difluoromethylenediphosphonate.

The 2',3'-O-isopropylidene-5-β-D-ribofuranosylnicotinamide (293 mg, 1 mmol), obtained as in Example 4, was dissolved in methylene chloride (6 mL), and then dimethylaminopyridine (122 mg, 1 mmol), triethylamine (202 mg, 2 mmol) and tosyl chloride (220, 1.2 mmol) was added. The mixture was stirred for 2 h and concentrated in vacuo. The residue was chromatographed on a column of silica gel with chloroform-ethanol (50:1, v/v) as the eluent to give 5'-O-tosyl derivative (410 mg, 92%). NMR (CDCl$_3$) δ 1.34 (s, 3H, iPr), 1.62 (s, 1H, iPr), 2.46 (s, 3H, Ts), 4.21 (dd, 1H, H5', J$_{4',5'}$=2.7 Hz, J$_{5',5''}$=10.8 Hz), 4.33–4.37 (m, 1H, H4'), 4.43 (dd, 1H, H5'', J$_{4',5''}$=2.6 Hz), 4.54 (pseudot, 1H, H3'), 4.74 (dd, 1H, H2', J$_{1',2}$=5.5 Hz, J$_{2',3}$=3.4 Hz), 5.01 (d, 1H, H1'), 5.71 (brs, 1H, NH$_2$), 6.72 (brs, 1H, NH$_2$), 7.37 (d, 2H, Ts, J=8.4 Hz), 7.78 (d, 2H, Ts), 8.25 (s, 1H, H4), 8.68 (brs, 1H, H6), 9.12 (brs, 1H, H2). A solution of 2',3'-O-isopropylidene-5'-O-tosyl-5-β-D-ribofuranosylnicotinamide (224 mg, 0.5 mmol) and tris(tetra-n-butylammonium) difluoromethylenediphosphonate (700 mg, 0.75 mmol) in dimethyl sulfoxide (10 mL) was kept standing for 2 h and lyophilized. The residue was dissolved in water and purified on preparative HPLC column as above to give 266 mg, 82% $^1$H NMR (D$_2$O) δ 1.42 (s, 3H, iPr), 1.67 (s, 3H, iPr), 4.27–4.33 (m, 2H, H5', H5''), 4.45–4.48 (m, 1H, H4'), 4.80–4.87 (m, 1H, H3'), 5.05–5.12 (m, 2H, H1', H2', J$_{1',2}$=5.7 Hz), 8.42 (s, 1H, H4), 8.73 (s, 1H, H6), 8.92 (s,1H, H2). $^{31}$P NMR (D$_2$), δ 4.12, 7.18 (part AB of ABX$_2$ system, J$_{A,B}$=52.0 Hz, J$_{A,X}$=88.5 Hz, J$_{B,X}$=73.2 Hz, X=F). $^{19}$F NMR (D$_2$) δ −53.61 (dd, 2F, J$_{P',F}$=88.5 Hz, J$_{P'',F}$=73.2 Hz).

By following the same procedure, but using the corresponding nucleoside of Formula II instead of nicotinamide riboside, the following difluoromethylenediphosphonates are prepared:
(6-β-D-Ribofuranosylpicolinamide-5'-yl) difluoromethylenediphosphonate,
(2-β-D-Ribofuranosylisonicotinamide-5'-yl) difluoromethylenediphosphonate,
(5-β-D-Ribofuranosyl-3-cyanopyridine-5'-yl) difluoromethylenediphosphonate,
(6-β-D-Ribofuranosyl-2-cyanopyridine-5'-yl) difluoromethylenediphosphonate, and
(2-(β-D-Ribofuranosyl-4-cyanopyridine-5'-yl) difluoromethylenediphosphonate.

EXAMPLE 6

(Adenosin-5'-yl)difluoromethylenediphosphonate.

5'-O-Tosyladenosine (421, 1 mmol) was treated with tris(terta-n-butylammonium) difluoromethylenediphosphonate as described in Example 5 to give the (adenosine-5-yl) difluoromethylenediphosphonate in 64% yield.

By following the same procedure, but using the corresponding nucleoside of Formula III instead of adenosine, the following difluoromethylenediphosphonates are prepared:
(2'-deoxyadenosin-5'-yl)difluoromethylenediphosphonate,
(2'-deoxy-2'-fluoroadenosin-5'-yl)difluoromethylenediphosphonate,
(3'-deoxy-3'-fluoroadenosin-5'-yl)difluoromethylenediphosphonate, and
[9-(2'-deoxy-2'-fluoro-β-D-arabinofuranosyl)adenine-5'-yl] difluoromethylenediphosphonate.

EXAMPLE 7

P$^1$-[5-(β-D-Ribofuranosyl)nicotinamide-5'-yl]-P$^2$-[adenosine-5''-yl]methylenediphosphonate and P$^1$-[(5-β-D-ribofuranosyl)-3-cyanopyridine-5'-yl]-P$^2$-[adenosine-5-yl] methylene-diphosphonate.

(Adenosine-5'-yl)methylenediphosphonate (obtained as in Example 4, . . . , 1 mmol) was dissolved in a mixture of DMSO (20 mL) and triethyl orthoformate (3.9 mL) and trifluoroacetic acid (5 mL) was added. The mixture was stirred for 16 h and lyophilized. The residue was treated with ethyl ether (100 mL). The precipitate was collected by centrifugation and dried at reduced pressure. This product was suspended in pyridine (16 mL) containing tri-n-butyl amine (2.5 mL) and 2',3'-O-isopropylidene-5-β-D-ribofuranose-nicotinamide (obtained as in Example 3, 322 mg, 1.1 mmol) and dicyclohexylcarbodiimide (DCC, 1.0 g) was added. The reaction was stirred for 4 days and concentrated in vacuo. The residue was suspended in water (100 mL), filtered and the filtrate was treated with Dowex 50 W (H$^+$) for 8 h. The resin was filtered, the filtrate was concentrated in vacuo and the residue was purified on preparative HPLC column as described before to give the β-methylene CNAD as triethylammonium salt, which was converted to the disodium salt by passing trough Dowex 50 W (Na$^+$) to give (60 mg, 10%). $^1$H NMR (D$_2$O) δ 2.28 (t, 2H, CH$_2$ J$_{P,H}$=20.1 Hz), 4.05–4.40 [m, 8H, H3',4',5',5'' (adenosine), H3',4',5',5'' (nicotinamide riboside)], 4.50 [pseudot, 1H, H2'(NR)], 4.70 [pseudot, 1H, H2'(A)], 4.87 [d, 1H, H1'(NR), J$_{1',2}$=4.9 Hz], 6.02 [d, 1H, H1' (A), J$_{1',2}$=5.2 Hz], 8.17 [s, 1H, H4 (NR)], 8.20, 8.45 [two 1H singlets, H2, H8 (A)], 8.59 [brs, 1H, H6(NR)], 8.75 [brs, 1H, H2 (NR)]. $^{31}$P NMR (D$_2$O) δ 17.63, 17.88 (AB system, J$_{A,B}$=10.4 Hz).

Due to dehydration (DCC) of the desired product, the P$^1$-[(5-β-D-ribofuranosyl)-3-cyanopyridine-5'-yl]-P$^2$-[adenosine-5'-yl]methylenediphosphonate (70 mg 14%) was also obtained. $^1$H NMR (D$_2$O) δ 2.28 (t, 2H, CH$_2$, J$_{P,H}$=20.1 Hz), 4.02–4.42 [m, 8H, H3',4',5',5'' (adenosine), H3',4',5',5'' (nicotinamide riboside)], 4.55 [pseudot, 1H, H2'(NR)], 4.74 [pseudot, 1H, H2'(A)], 4.79 [d, 1H, H1'(NR), J$_{1',2}$=4.9 Hz], 6.06 [d, 1H, H1' (A), J$_{1',2}$=5.4 Hz], 8.17 [s, 1H, H4 (NR)], 8.20, 8.50 [two 1H singlets, H2, H8 (A)], 8.69 [s, 1H, H6 (NR)], 8.71 [s, 1H, H2 (NR)]. $^{31}$P NMR (D$_2$O) δ 17.63, 17.88 (AB system, J$_{A,B}$=9.9 Hz).

By following the same procedure, but using the corresponding methylenediphosphonates of the compound of Formula III instead of (adenosin-5'-yl) methylenediphosphonate and nucleosides of Formula II, the following dinucleotides are prepared:
P$^1$-[6-(β-D-Ribofuranosyl)picolinamide-5'-y]-P$^2$-[adenosine-5''-yl]methylenediphosphonate,
P$^1$-[2-(β-D-Ribofuranosyl)isonicotinamide-5'-yl]-P$^2$-[adenosine-5''-yl]methylenediphosphonate P$^1$-[5-(β-D-Ribofuranosyl)-3-cyanopyridine-5'-yl]-P$^2$-[adenosine-5''-yl]methylenediphosphonate,
P$^1$-[6-(β-D-Ribofuranosyl)-2-cyanopyridine-5'-yl]-P$^2$-[adenosine-5''-yl]methylenediphosphonate,
P$^1$-[2-(β-D-Ribofuranosyl)-4-cyanopyridine-5'-yl]-P$^2$-[adenosine-5''-yl]methylenediphosphonate,
P$^1$-[5-(β-D-Ribofuranosyl)nicotinamide-5'-yl]-P$^2$-[2'-deoxyadenosine-5''-yl]methylenediphosphonate,
P$^1$-[6-(β-D-Ribofuranosyl)picolinamide-5'-yl]-P$^2$-[2'-deoxyadenosine-5''-yl]methylenediphosphonate, P¹-[2-(β-D-Ribofuranosyl)isonicotinamide-5'-yl]-P²-[2'-deoxyadenosine-5"-yl]methylenediphosphonate, P¹-[5-(β-D-Ribofuranosyl)-3-cyanopyridine-5'-yl]P²-[2'-deoxyadenosine-5"-yl]methylenediphosphonate, P¹-[6-(β-D-Ribofuranosyl)-2-cyanopyridine-5'-yl]-P²-2'-deoxyadenosine-5"-yl]methylenediphosphonate, P¹-[2-(β-D-Ribofuranosyl)-4-cyanopyridine-5'-yl]-P²-[2'-deoxyadenosine-5"-yl]methylenediphosphonate, P¹-[5-(β-D-Ribofuranosyl)nicotinamide-5'-yl]-P²-[2'-deoxy-2'-fluoroadenosine-5"-yl]methylenediphosphonate, P¹-[6-(β-D-Ribofuranosyl)picolinamide-5'-yl]-P²-[2'-deoxy-2'-fluoroadenosine-5"-yl]methylenediphosphonate, P¹-[2-(β-D-Ribofuranosyl)isonicotinamide-5'-yl]-P²-[2'-deoxy-2'-fluoroadenosine-5"-yl]methylenediphosphonate, P¹-[5-(β-D-Ribofuranosyl)-3-cyanopyridine-5'-yl]-P²-[2'-deoxy-2'-fluoroadenosine-5"-yl]methylenediphosphonate, P¹-[6-(β-D-Ribofuranosyl)-2-cyanopyridine-5'-yl]-P²-[2'-deoxy-2'-fluoroadenosine-5"-yl]methylenediphosphonate, P¹-[2-(β-D-Ribofuranosyl)-4-cyanopyridine-5'-yl]-P²-[2'-deoxy-2'-fluoroadenosine-5"-yl]methylenediphosphonate, P¹-[5-(β-D-Ribofuranosyl)nicotinamide-5'-yl]-P²-[3'-deoxy-3'-fluoroadenosine-5"-yl]methylenediphosphonate, P¹-[6-(β-D-Ribofuranosyl)picolinamide-5'-yl]-P²-[3'-deoxy-3'-fluoroadenosine-5"-yl]methylenediphosphonate, P¹-[(β-D-Ribofuranosyl)isonicotinamide-5'-yl]-P²-[3'-deoxy-3'-fluoroadenosine-5"-yl]methylenediphosphonate, P¹-[5-(β-D-Ribofuranosyl)-3-cyanopyridine-5'-yl]-P²-[3'-deoxy-3'-fluoroadenosine-5"-yl]methylenediphosphonate, P¹-[6-(β-D-Ribofuranosyl)-2-cyanopyridine-5'-yl]-P²-[3'-deoxy-3'-fluoroadenosine-5"-yl]methylenediphosphonate, P¹-[2-(β-D-Ribofuranosyl)-4-cyanopyridine-5'-yl]-P²-[3'-deoxy-3'-fluoroadenosine-5"-yl]methylenediphosphonate, P¹-[5-(β-D-Ribofuranosyl)nicotinamide-5'-yl]-P²-[9-(2'-deoxy-2'-fluoro-β-D-arabinofuranosyl)adenine-5"-yl]methylenediphosphonate, P¹-[6-(β-D-Ribofuranosyl)picolinamide-5'-yl]-P²-[9-(2'-deoxy-2'-fluoro-β-D-arabinofuranosyl)adenine-5"-yl]methylenediphosphonate, P¹-[2-(β-D-Ribofuranosyl)isonicotinamide-5'-yl]-P²-[9-(2'-deoxy-2'-fluoro-β-D-arabinofuranosyl)adenine-5"-y]methylenediphosphonate, P¹-[5-(β-D-Ribofuranosyl)-3-cyanopyridine-5'-yl]-P²-[9-(2'-deoxy-2'-fluoro-β-D-arabinofuranosyl)adenine-5"-yl]methylenediphosphonate, P¹-[6-(β-D-Ribofuranosyl)-2-cyanopyridine-5'-yl]-P²-[9-(2'-deoxy-2'-fluoro-β-D-arabinofuranosyl)adenine-5"-yl]methylenediphosphonate, and P¹-[2-(β-D-Ribofuranosyl)-4-cyanopyridine-5'-yl]-P²-[9-(2'-deoxy-2'fluoro-β-D-arabinofuranosyl)adenine-5"-yl]methylenediphosphonate,

EXAMPLE 8

P¹-[5-(β-D-Ribofuranosyl)nicotinamide-5'-yl]-P² [adenosine-5"-yl]difluoromethylenedi-phosphonate.

The (2',3'-O-isopropylidene-5-β-D-ribofuranosylnicotinamide-5'-yl) difluoromethylenediphosphonate (obtained as in Example 5, 649 mg, 1 mmol) was coupled with 2',3'-O-isopropylidene adenosine (4.6 g, 15 mmol) in the same manner as above to give β-difluoromethylene CNAD (50, 7%) ¹H NMR (D₂O) 4.05–4.40 (m, 8H, H3', H4', H5', H5" –A and NR), 4.53 (pseudot, 1H, H2' (NR), 468 (pseudot, 1H (A), 4.90 (d, 1H, H1' (NR), $J_{1',2}$=5.1 Hz), 5.99 (d, 1H, H1' (A), $J_{1',2}$=5.3 Hz), 8.21 (s, 1H, H4 (NR)], 8.26, 8.50 [two 1H singlets, H2, H8 (A)], 8.61 (s, 1H, H6 (NR)], 8.80 (s, 1H, H2 (NR)]. ³¹P NMR (D₂O) δ 4.02, 4.36 (AB part of ABX₂ system, $J_{A,B}$= 55.3 Hz, $J_{A,X}$=83.1 Hz, $J_{B,X}$=83.5 Hz, X=F).

By following the same procedure, but using the corresponding difluoromethylenediphosphonate derivative of the compound of Formula II instead of (5-β-D-ribofuranosylnicotinamide-5'-yl) difluoromethylenediphosphonate and nucleosides of Formula III, the following dinucleotides are prepared:

P¹-[6-(β-D-Ribofuranosyl)picolinamide-5'-yl]-P²-[adenosine-5"-yl]difluoromethylenediphosphate, P¹-[2-(β-D-Ribofuranosyl)isonicotinamide-5'-yl]-P²-[adenosine-5"-yl]difluoromethylenediphosphonate, P¹-[5-(β-D-Ribofuranosyl)-3-cyanopyridine-5'-yl]-P²-[adenosine-5"-yl]difluoromethylenediphosphonate, P¹-[6-(β-D-Ribofuranosyl)-2-cyanopyridine-5'-yl]-P²-[adenosine-5"-yl]difluoromethylenediphosphonate, P¹-[2-(β-D-Ribofuranosyl)-4-cyanopyridine-5'-yl]-P²-[adenosine-5"-yl]difluoromethylenediphosphonate, P¹-[5-(β-D-Ribofuranosyl)nicotinamide-5'-yl]-P²-[2'-deoxyadenosine-5"-yl]difluoromethylenediphosphonate, P¹-[6-(β-D-Ribofuranosyl)picolinamide-5'-yl]-P²- [2'-deoxyadenosine-5"-yl]difluoromethylenediphosphonate, P¹-[2-(β-D-Ribofuranosyl)isonicotinamide-5'-yl]-P²-[2'-deoxyadenosine-5"-yl]difluoromethylenediphosphonate, P¹-[5-(β-D-Ribofuranosyl)-3-cyanopyridine-5'-yl]P²-[2'-deoxyadenosine-5"-yl]difluoromethylenediphosphonate, P¹-[6-(β-D-Ribofuranosyl)-2-cyanopyridine-5'-yl]-P²-2'-deoxyadenosine-5"-yl]difluoromethylenediphosphonate, P¹-[2-(β-D-Ribofuranosyl)-4-cyanopyridine-5'-yl]-P²-[2'-deoxyadenosine-5"-yl]difluoromethylenediphosphonate, P¹-[5-(β-D-Ribofuranosyl)nicotinamide-5'-yl]-P²-[2'-deoxy-2'-fluoroadenosine-5"-yl]difluoromethylenediphosphonate, P¹-[6-(β-D-Ribofuranosyl)picolinamide-5'-yl]-P²-[2'-deoxy-2'-fluoroadenosine-5"-yl]difluoromethylenediphosphonate, P¹-[2-(β-D-Ribofuranosyl)isonicotinamide-5'-yl]-P²-[2'-deoxy-2'-fluoroadenosine-5"-yl]difluoromethylenediphosphonate, P¹-[5-(β-D-Ribofuranosyl)-3-cyanopyridine-5'-yl]-P²-[2'-deoxy-2'-fluoroadenosine-5"-yl]difluoromethylenediphosphonate, P¹-[6-(β-D-Ribofuranosyl)-2-cyanopyridine-5'-yl]-P²-[2'-deoxy-2'-fluoroadenosine-5"-yl]difluoromethylenediphosphonate, P¹-[2-(β-D-Ribofuranosyl)-4-cyanopyridine-5'-yl]-P²-[2'-deoxy-2'-fluoroadenosine-5"-yl]difluoromethylenediphosphonate, P¹-[5-(β-D-Ribofuranosyl)nicotinamide-5'-yl]-P²-[3'-deoxy-3'-fluoroadenosine-5"-yl]difluoromethylenediphosphonate, P¹-[6-(β-D-Ribofuranosyl)picolinamide-5'-yl]-P²-[3'-deoxy-3'-fluoroadenosine-5"-yl]difluoromethylenediphosphonate, P¹-(β-D-Ribofuranosyl)isonicotinamide-5'-yl-P²-3'-deoxy3'-fluoroadenosine-5"-yl-fluoro]difluoromethylene-diphosphonate, P¹-[5-(β-D-Ribofuranosyl)-3-cyanopyridine-5'-yl]-P²-[3'-deoxy-3'-fluoroadenosine-5"-yl]difluoromethylenediphosphonate, P¹-[6-(β-D-Ribofuranosyl)-2-cyanopyridine-5'-yl]-P²-[3'-deoxy-3'-fluoroadenosine-5"-yl] difluoromethylenediphosphonate, P¹-[2-(β-D-Ribofuranosyl)-4-cyanopyridine-5'-yl]-P²-[3'-deoxy-3'-fluoroadenosine-5"-yl] difluoromethylenediphosphonate, P¹-[5-(β-D-Ribofuranosyl)nicotinamide-5'-yl]-P²-[9-(2'-deoxy-2'-fluoro-β-D-arabino-furanosyl)]adenine-5"-yl] difluoromethylenediphosphonate, P¹-[6-(β-D-Ribofuranosyl)picolinamide-5'-yl]-P²-[9-(2'-deoxy-2'-fluoro-β-D-arabino-furanosyl)]adenine-5"-yl] difluoromethylenediphosphonate, P¹-[2-(β-D-Ribofuranosyl)isonicotinamide-5'-yl]-P²-[9-(2'-deoxy-2'-fluoro-β-D-arabino-furanosyl)adenine-5"-yl] difluoromethylenediphosphonate, P¹-[5-(β-D-Ribofuranosyl)-3-cyanopyridine-5'-yl]-P²-[9-(2'-deoxy-2'-fluoro-β-D-arabino-furanosyl)adenine-5"-yl]difluoromethylenediphosphonate, P¹-[6-(β-D-Ribofuranosyl)-2-cyanopyridine-5'-yl]-P²-[9-(2'-deoxy-2'-fluoro-β-D-arabino-furanosyl)adenine-5"-yl]difluoromethylenediphosphonate, and P¹-[2-(β-D-Ribofuranosyl)-4-cyanopyridine-5'-yl]-P²-[9-(2'-deoxy-2'-fluoro-β-D-arabino-furanosyl)adenine-5"-yl]difluoromethylenediphosphonate.

Biological Activity

1. Cytoxicity of 5-(β-D-ribofuranosyl)nicotinamide-(5'-5")-adenosine pyrophosphate (Compound 2, CNAD) to murine leukemia L1210 cells.

Murine leukemia L1210 cells were grown in RPMI 1640 medium. Logarithmically growing cells were incubated with various concentrations of CNAD for 24 and 48 hr periods and the cytoxicity determined by counting the cells in a Coulter counter.

It was found that the 5-(β-D-ribofuranosyl)nicotinamide-(5'-5")-adenosine pyrophosphate (Compound 2, CNAD) inhibits the proliferation of L1210 cells by 50% ($IC_{50}$) at the concentration of 7 μM.

2. Inhibition of horse liver alcohol dehydrogenase (ADH) and bovine glutamate dehydrogenase (GDH)

Rate measurements for each of the dehydrogenases used in this study are based on the spectral properties of NADH. In assays with NAD as a substrate, rates were determined by measuring the increase in absorbance at 340 nm resulting from the conversion of NAD to NADH. Rates, using absorbance measurements, were calculated using a millimolar extinction coefficient of 6.22/cm for NADH.

Alcohol dehydrogenase assays were run at pH 8.0, using 0.1M sodium phosphate buffer. Glutamate dehydrogenase assays were at pH 7.0 in 0.1M sodium phosphate buffer, containing 10 μm EDTA. All kinetic assays were run at least in duplicate.

Initial values of inhibition constants were estimated from Lineweaver-Burk plots, using linear regression to obtain values for the slope and intercept of each line. Inhibition was judged to be competitive if the values obtained for the intercepts of the appropriate polots differed by less than three standard deviations as determined by linear regression. Values for the inhibition constant, $K_{is}$ was obtained using the relationship:

$$K_{is}=[I]/\{[S(+)/S(-)]-1\}$$

where S(+) and S(−) are the slopes of the plots in the presence and absence of inhibitor, respectively, and [I] is the concentration of total added inhibitor. Where a noncompetitive pattern of inhibition was observed, a similar analysis was used to obtain $K_{ii}$. $K_m$ for conenzyme was obtained from the slope and intercept obtained in plots in the absence of inhibitor, using the relationship: $K_m$=Slope/$V_{max}$.

Values of effective inhibition constants and patterns of inhibition for CNAD binding to ADH were obtained by direct least-squares fits to the nonreciprocal forms of the Michaelis-Menten rate equations. Kinetic data were fit to the following relationships, assuming both competitive and non-competitive inhibition respectively:

$$v_o=V_m[A]/\{K_m(1+[I]/K_{is})+[A]\}$$

or $$v_o=V_m[A]/\{K_m(1+[I]/K_{is})+[A](1+[I]/K_{ii})\}$$

Where $v_o$ is the initial reaction rate, $V_m$ is the maximal rate, and $K_m$ and [A] the Michaelis constant and concentration of the variable substrate, respectively. The pattern of inhibition considered to best account for the observed data was that giving both the smallest residuals between observed and calculated values, and the smallest standard errors in the computed kinetics constants. This method demonstrated non-competitive inhibition of ADH with respect to NAD by CNAD with an apparent $K_i$ ($K_i'$) of 6 nM.

In order to estimate the magnitude of nonlinear effects introduced by tight binding by CNAD, apparent $K_i$'s with respect to NAD were also obtained by a fit of kinetic data to Sculley and Morrison's nonlinear rate equation:

$$v_o=\frac{k_{cat}[A]}{2(Km+[A])}[\{([E]-[I]-K_i)^2+4K_i\}^{1/2}-(K_i+[I]-[E])]$$

where [E] is the total enzyme concentration, $k_{cat}$ is the maximum rate of product formation and, in this case, [A] is the concentration and Km the Michaelis constant of NAD. Derivation of this rate equation assumes the presence of a tight binding inhibitor, i.e., that [I]~[E].

In this experiment both inhibitor and enzyme concentration were varied. Initial rates $v_o$ were measured at total concentrations of CNAD ([I]) of 0, 2.4, 9.6, and 19.2 nM over four concentrations of ADH ([E]). Concentrations of ethanol and NAD were fixed at 1.2 nM and 87 μM at pH 8.0. The apparent inhibition constant with respect to NAD, $K_i'$, was then obtained by non-linear least-squares fit to the rate equation under the array of experimental conditions employed. The true rate constant $K_i$ was obtained from the apparent rate constant $K_i'$ was obtained from the apparent rate constant $K_i$, via the relationship:

$$K_i=K_i'/(1+[A]/K_m)$$

Results for 6-(β-D-ribofuranosyl)picolinamide-(5'–5") adenosine pyrophosphate (C-PAD)indicate competitive inhibition of ADH with respect to NAD, with $K_i$=20 μM. The results for CNAD, however, showed competitive inhibition of GDH ($K_i$=15 μM), but non-competitive inhibition of ADH, with $K_i$=2 nM.

Discussion

Inhibition of alcohol dehydrogenase (ADH) provides potential therapies for ethylene glycol intoxication, ethanol-induced hypoglycemia and lactacidemia and methanol poisoning. This along with the extensive structural information available about the enzyme and its complexes, have made ADH an attractive target for inhibitor design. A number of classes of highly potent reversible ADH-inhibitors have been developed. These are 4-substituted alkylpyrazoles, 1-mercapto-n-alkanes, phenylacetamide and formamide derivatives and adloximes. Like CNAD, these inhibitors bind the catalytic site Zn via a nitrogen, oxygen or sulfur ligand. Unlike CNAD, these compounds act as substrate analogues, binding Zn from the substrate site, with alkyl or phenyl groups extending into the hydrophobic substrate cleft. Inhibitors of this type can bind in-ternary complexes with cofactor, forming a secondary ligand to the nicotinamide ring. NAD analogues have been developed as inactivating affinity labels, forming covalent interactions with active site residues. However, CNAD is the first cofactor analogue which reversibly interacts with the catalytic Zn.

Similar selectivity for these compounds is asserted for inosine monophosphate dehydrogenase (IMPDH). As a result, such NAD analogues should be valuable in cancer treatment. NAD-analogues, not nucleosides, that are able to penetrate the cell membrane may be of therapeutic interest since nucleosides related to nicotinamide riboside are not effectively metabolized into their corresponding NAD-analogues. They do not require metabolic activation by cellular enzymes.

EXAMPLE 9

A. Introduction.

X-ray structure determination of a number dehydrogenase-NAD complexes indicate that the 2'- and 3'-hydroxy groups of both furanose rings of the cofactor participate in hydrogen bonds which help anchor the ligand within the active site.(17–20) In LADH, initial recognition of the cofactor appears to occur via binding to the adenine end,(21) which requires a C2' endo conformation of the adenosine ribose.(20) Other dehydrogenases require a C3' endo conformation at this end of the cofactor.(18,28)

In IMPDH and LADH, TAD displaces NAD binding at the cofactor site.(20,22) We therefore suspected that TAD analogues containing fluorine substituents, such as 2'-fluoro- and 3'-fluoro substituted adenine nucleosides, would provide probes of the stereochemical requirements of the adenine end of the cofactor site on IMPDH. Fluorine acts as even stronger hydrogen bond acceptor than a hydroxyl oxygen, but does not serve as hydrogen bond donor. The carbon-fluorine bond length, 1.39 A, closely resembles the carbon-oxygen bond length, 1.43 A. However, fluorine is a less sterically demanding substituent than the hydroxyl group having Van der Waals radius (1.35 A) similar to that of hydrogen (1.29 A). Replacement of the ribose hydroxyl group by fluorine can constrain the sugar conformation and improve its transport properties. For example, 2'-deoxy-2'-fluoroadenosine is a unique analogue of adenosine, which exhibits a number of interesting biological activities.(25–27) In this analogue, the ribose ring is in a C3'-endo conformation due to the highly electronegative 2'-substituent.(24) In contrast, 3'-deoxy-3'-fluoroadenosine (29,30,31) favors the C2'-endo sugar pucker.(29)

Similarly, TAD analogues with a fluorine substituent at either the C2'or C3' will demonstrate differences in preferred sugar conformation and hydrogen bonding capabilities. However, little is known of the importance of the configuration of adenosine hydroxyl groups on the NAD binding in IMPDH. It has been reported that replacement of the nicotinamide riboside of NAD by 2'-deoxy-2'-fluoro-arabinose yielded an active cofactor in at least one system.(32) Thus, the relative affinities of all fluorine analogues are of interest.

TAD analogues substituted with fluorine in the ribose moiety of adenosine are also more hydrophobic than their corresponding hydroxy congeners. The increased liphophilicity of fluorine substituted TAD analogues in comparison with unmodified TAD is well expressed by their substantially longer retention times on reverse phase HPLC. This feature would be crucial in the activity of TAD analogues, which must be able to penetrate cell membranes. The β-methylene TAD (33) (β-$CH_2$-TAD, Chart I) as well as β-difluoromethylene TAD (34) (β-$CF_2$-TAD) recently synthesized by us, can penetrate cell membranes although not as efficiently as tiazofurin.(3S) Lastly, fluorinated TAD derivatives are potentially less toxic than the parent compound. Fluorinated TAD analogues which do not contain the 2'-hydroxyl function of the adenosine moiety cannot be converted into the corresponding NADP analogue by cellular enzyme(s). Thus the fluroinate TAD analogues should be less toxic than TAD itself, since the former should be harmless toward numerous NADP-dependent cellular enzymes.

In the following Experimental details we report the synthesis of three TAD analogues containing a fluorine atom at the C2', in the ribo and arabino configuration, or at the C3', in the ribo configuration, of the adenine nucleoside. We also report the results of inhibitory activity studies of our TAD analogues as well as β-$CF_2$-TAD against the tumor-dominant IMPDH type II.

The three analogues of thiazole-4-carboxamide adenine dinucleotide containing a fluorine atom at the C2' of the adenine nucleoside, in the ribo and arabino configuration, and at the C3', in the ribo configuration, were synthesized in high yield from the corresponding 5'-monophosphates of 2'-deoxy-2'-fluoroadenosine (Compound 11), 9-(2-deoxy-2-fluoro-β-D-arabinofuranosyl)adenine (Compound 19), and 3'-deoxy-3'-fluoroadenosine (Compound 16), respectively. Pure 2',3'-O-isopropylidenetiazofurin 5'-phosphorimidazolide (Compound 10) was obtained by phosphorylation of the protected tiazofurin followed by treatment with carbonyldiimidazole and HPLC purification. Reaction of Compound 10 with Compound 11 in DMF-$d_7$ (monitored by $^1$H and $^{31}$P NMR) afforded the desired dinucleotide Compound 14, which after deisopropylidenation gave Compound 3 in 82% yield. Small amounts of symmetrical dinucleotides AppA (Compound 12, 7.2%) and TRppTR (Compound 13, 8.0%) were also isolated during HPLC purification of the major product Compound 14. In a similar manner Compounds 4 and 5 were obtained by coupling of Compound 10 with Compounds 16 and 19 in 80% and 76% yield, respectively. All newly prepared fluoro substituted compounds as well as β-$CF_2$-TAD, earlier synthesized by us, showed good inhibitory activity against inosine monophosphate dehydrogenase type II, the isozyme which is predominant in neoplastic cells. Binding of Compound 3 ($K_{is}$=0.5 μM), Compound 4 ($K_{is}$=0.7 μM), and Compound 5 ($K_{is}$=2.9 μM) was comparable to that of TAD ($K_i$=0.2 μM). The difluoromethylene bisphosphonate analogue, β-$CF_2$-TAD ($K_i$=0.17 μM), was found to be equally effective as the best cofactor-type inhibitor β-$CH_2$-TAD ($k_i$=0.11 μM). Interestingly, the level of inhibition of horse liver alcohol dehydrogenase (LADH) by these compounds was found to be much lower (0.1 mM for Compounds 3 and 4 and no inhibition up to 10 mM for Compound 5). These findings show that inhibition of tumor induced IMPDH type II is selective and may be of therapeutic interest.

B. General Methods.

Melting points were determined on a Thomas-Hoover capillary apparatus and are uncorrected. HPLC was performed an a Dynamax-60A C18-83-221-C column with flow rate of 5 mL/min or Dynamax-300A C18-83-243-C column with a flow rate of 20 mL/min of 0.1M $Et_3N$ $H_2CO_3$ (TEAB) followed by a linear gradient of 0.1M TEAB-aq.MeCN (70%). Elemental analyses were performed by M-H-W Laboratories, Phoenix, Ariz. Nuclear magnetic resonance spectra were recorded on a Bruker AMX-250 and -400 spectrometer with Me$_4$Si or DDS as the internal standard for $^1$H and $^{13}$C and external H$_3$PO$_4$ for $^{31}$P. Chemical shifts are reported in ppm (δ) and signals are described as s (singlet), d (doublet), t (triplet), q (quartet), m (multiplet), bs (broad singlet), and dd (double doublet). Values given for coupling constants are first order.

C. Preparation of Compounds.

Reaction schemes 1 and 2 and the structures of representative compounds discussed below can be found in Table 1 following the discussion of the preparation of the compounds.

1. Reaction of AMP with 1,1'-carbonyldiimidazole.

To a solution of adenosine 5'-monophosphate monohydrate (Compound 6, 36.5 mg, 0.1 mmol) in Me$_2$SO-d$_6$ (1 mL) was added CDI (76 mg, 0.4 mmol) and the reaction was monitored using $^{31}$P and $^1$H NMR. After 3 min, the $^{31}$P resonance signal of Compound 6 at δ 1.75 disappeared and a singlet of intermediate [A] emerged at δ–5.71. $^1$H NMR of Compound 6 δ 3.97 (dd, 1H, H5", J$_{4',5"}$=6.10 Hz, J$_{5',5"}$= 12.20 Hz), 4.04–4.08 (m, 2H, H4', H5'), 4.16–4.20 (m, 1H, H3'), 4.59 (pseudo t, 1H, H2'), 5.42 (brs, 4H, 4×OH), 5.92 (d, 1H, H1', J$_{1',2}$=5.75 Hz), 7.43 (s, 2H, NH$_2$), 8.17, 8.35 (two 1H singlets, H2, H8). $^1$H NMR of [A] δ 4.10–4.12 (m, 3H, H4', H5', H5"), 4.22 (m, 1H, H3'), 4.62 (pseudo t, 1H, H2'), 5.95 (d, 1H, H1', J$_{1',2}$=5.96 Hz), 6.69 (brs, 3×OH), 6.99, 7.27, 7.48 (three 1H singlets, imidazole), 7.34 (s, 2H, NH$_2$), 8.14, 8.43 (two 1H singlets, H2, H8), 7.20, 7.78, 8.36 (three singlets of excess CDI). After 20 min, intermediate [A] remained a major component (70%) of the reaction mixture but two new resonance signals i.e. a singlet of intermediate [B] (16%) at δ–6.09 and a singlet of Compound 7 (14%) at δ–7.76 appeared. After 1 h, the reaction mixture contained four compounds: [A] (7%), [B] (12%), Compound 7 (26%), and Compound 8 (55%, singlet at δ–7.75), and after 2.5 h, Compound 8 was the only product detected. $^1$H NMR δ 3.72–3.83 (m, 2H, H5', H5"), 4.41–4.45 (m, 1H, H4'), 5.44 (dd, 1H, H3', J$_{2',3}$=7.7 Hz, J$_{3',4}$=3.2 Hz), 5.93 (dd, 1H, H2', J$_{1',2}$=2.3 Hz), 6.46 (dd, 1H, H1), 6.92, 7.19, 7.77 (three 1H singlets, imidazole), 7.48 (s, 2H, NH$_2$), 8.12, 8.32 (two 1H singlets, H2, H8), 7.10, 7.84 (two singlets of the free imidazole). The mixture was then lyophilized and the residue was chromatographed on an HPLC column to give Compound 7 (10 mg, 20%) and an approximately 9:1 mixture of Compounds 8 and 7 (45 mg). This mixture was dissolved in water-Et$_3$N (pH=9), kept at room temperature for 2 h and concentrated in vacuo to give Compound 7 (33 mg). Total yield of Compound 7 was 43 mg, 100%, $^1$H NMR (Me$_2$SO-d$_6$) δ 1.00 (t, 9H, Et$_3$N), 2.70 (q, 6H, Et$_3$N), 3.60–3.76 (m, 2H, H5', H5"), 3.89–3.91 (m, 1H, H4'), 3.99–4.06 (m, 1H, H3'), 4.57 (pseudo t, 1H, H2'), 5.88 (d, 1H, H1', J$_{1',2}$=6.1 Hz), 6.85, 7.10, 7.65 (three 1H singlets, imidazole), 7.25 (s, 2H, NH$_2$), 8.12, 8.40 (two 1H singlets, H2, H8).

2. 2',3'-O-Isopropylidenetiazofurin 5'-monophosphate (Compound 9) and 2-(2,3-O-isopropylidene-β-D-ribofuranosyl)thiazole-4-carbonitrile 5'-monophosphate (Compound 9a). (47)

To a suspension of 2',3'-O-isopropylidenetiazofurin$^4$ (300 mg, 1 mmol) in triethyl phosphate (2 mL) was added a mixture of (EtO)$_3$PO (2 mL) containing water (20 µL) and P(O)Cl$_3$ (200 µL). The mixture was kept at 5°–10° C. for 20 h and then added dropwise into a solution of 2M TEAB (6 mL) in water (100 mL). Extraction with EtOAc (2×50 mL) and concentration of aqueous layer in vacuo gave the residue which was further purified on HPLC column. After lyophilization two compounds were obtained: faster migrating Compound 9 as mono triethylammonium salt (240 mg, 50%), $^{31}$P NMR (D$_2$O) δ 0.64 (t, J$_{5',5"}$,$_P$=5.5 Hz), 1H NMR (D$_2$O) δ 1.29 (t, 9H, Et$_3$N), 1.46 (s, 3H, iPr), 1.66 (s, 3H, iPr), 3.19 (q, 6H, Et$_3$N), 3.99 (pseudo t, 2H, H5', H5"), 4.56–4.60 (m,1H, H4'), 5.02 (dd, 1H, H3', J$_{2',3}$=6.1 Hz, J$_{3',4}$=2.3 Hz), 5.20 (dd, 1H, H2', J$_{1',2}$=4.0 Hz), 5.38 (d, 1H, H1'), 8.27 (s, 1H, H5). $^{13}$C NMR (D$_2$O) δ 11.11 (Et$_3$N), 27.32 (iPr), 29.10 (iPr), 49.51 (Et$_3$N), 67.74 (d, C5', J$_{C,P}$=4.9 Hz), 85.00 (C2'), 86.87 (C3'), 87.14 (C4', d, J$_{C,P}$=9.0 Hz), 87.77 (C1'), 117.70 (iPr), 129.47 (C5), 151.00 (C4), 168.28 (C=O), 173.76 (C2), and slower migrating Compound 9a (138 mg, 30%, triethylammonium salt). $^{31}$P NMR (D$_2$O) δ 0.58 (dt, J$_{5',5"}$,$_P$=5.6 Hz, J$_{4',P}$=1.8 Hz), $^1$H NMR (D$_2$O) δ 1.29 (t, 9H, Et$_3$N), 1.45 (s, 3H, iPr), 1.65 (s, 3H, iPr), 3.19 (q, 6H, Et$_3$N), 3.98 (pseudo t, 2H, H5', H5"), 4.59–4.62 (m,1H, H5'), 5.03 (dd, 1H, H3', J$_{2',3}$=6.0 Hz, J$_{3',4}$=2.0 Hz), 5.20 (dd, 1H, H2', J$_{1',2}$=3.8 Hz), 5.38 (d, 1H, H1,), 8.48 (s, 1H, H5). $^{13}$C NMR (D$_2$O) δ 11.11 (Et$_3$N), 27.30 (iPr), 29.10 (iPr), 49.51 (Et$_3$N), 67.94 (d, C5', J$_{C,P}$=4.8 Hz), 85.21 (C2'), 87.30 (C3'), 87.42 (C4', d, J$_{C,P}$=9.2 Hz), 87.94 (C1), 117.00 (CN), 117.55 (iPr), 127.82 (C4), 136.99 (C5), 176.37 (C2).

3. 2',3'-O-Isopropylidenetiazofurin5'-phosphoimidazolide (Compound 10).

Nucleotide compound 9 (96 mg, 0.20 mmol as mono triethylammonium salt) was dissolved in DMF-d$_7$ (1 mL). CDI (33 mg, 0.22 mmol) was added and progress of the reaction was monitored by $^{31}$P NMR. The resonance signal of Compound 9 (δ 1.63) disappeared and the new signal of intermediate [A] emerged at δ –6.53, which diminished in time with simultaneous formation of the resonance of the imidazolide derivative Compound 10 (δ –7.79). After 30–40 min, the reaction was completed, the mixture was lyophilized, the residue was dissolved in 0.1M TEAB (3 mL) and purified by HPLC to give nucleotide imidazolide Compound 10 (100 mg, 94%, triethylammonium salt). $^{31}$P NMR (D$_2$O) δ –7.80. $^1$H NMR (D$_2$O) δ 1.42 (s, 3H, iPr), 1.61 (s, 3H, iPr), 3.92–3.97 (m, 2H, H5', H5"), 4.42–4.57 (m, 1H, H4'), 4.79–4.81 (m, 1H, H3'), 5.18 (dd, 1H, H2', J$_{1',2}$=3.4 Hz, J$_{2',3}$=6.0 Hz), 5.33 (d, 1H, H1'), 7.03, 7.11, 7.75 (three 1H singlets, imidazole), 8.17 (s, 1H, H5).

4. 2'-Deoxy-2'-fluoroadenosine 5'-monophosphate (Compound 11). (49)

The 2'-deoxy-2'-fluoroadenosine (269 mg, 1 mmol) was treated with P (O)Cl$_3$ in the same manner as 2',3'-O-isopropylidene-tiazofurin to give Compound 11, as its triethylammonium salt, in 78% yield. $^{31}$P NMR (D$_2$O), δ 0.90, $^1$H NMR (D$_2$O), δ 1.27 (t, 9H, Et$_3$N), 3.19 (q, 6H, Et$_3$N), 4.15 and 4.27 (dd of AB system, 2H, H5', H5", J$_{5',5"}$=12.0 Hz, J$_{4',5}$=3.0 Hz, J$_{H}$5'.P=5.5 Hz, J$_{4',5"}$=2.4 Hz, J$_{5",P}$=4.5 Hz), 4.34–4.42 (m, 1H, H4'), 4.69 (ddd, 1H, H3', J$_{2',3}$=4.4 Hz, J$_{3',4}$=7.4 Hz, J$_{3',F}$=20.0 Hz), 5.40 (ddd, 1H, H2', J$_{1',2}$=2.15 Hz, J$_{2',F}$=52.0 Hz), 6.39 (dd, 1H, H1', J$_{1',F}$=16.2 Hz), 8.22 and 8.41 (two 1H singlets, H2, H8). Anal. (C$_{16}$H$_{28}$FN$_6$O$_6$P× 3H$_2$O) C, H, N.

5. 3'-Deoxy-3'-fluoroadenosine 5'-monophosphate (Compound 16). (50)

The compound was prepared, as triethylamonium salt, as above from 3'-deoxy-3'-fluoroadenosine (269 mg, 1 mmol) in 65% yield. $^{31}$P NMR (D$_2$O), δ 0.74, $^1$H NMR (D$_2$O), δ 1.26 (t, 9H, Et$_3$N), 3.18 (q, 6H, Et$_3$N), 4.08 and 4.16 (m and dd of AB system, 2H, H5', H5", J$_{5',5"}$=11.8 Hz, J$_{4',5}$=2.5 Hz, J$_{5",P}$=5.2 Hz), 4.62–4.78 (d of m, 1H, H4', J$_{4',F}$=27.4 Hz), 4.92 (ddd, 1H, H2', J$_{1',2}$=8.2 Hz, J$_{2',3}$=4.5 Hz, J$_{2',F}$=25.0 Hz), 5.31 (dd, 1H, H3', J$_{3',F}$=53.7 Hz), 6.16 (d, 1H, H1'), 8.19 and 8.48 (two 1H singlets, H2, H8). Anal. (C$_{16}$H$_{28}$FN$_6$O$_6$P×3H$_2$O) C, H, N.

6. 9-(2-Deoxy-2-fluoro-β-D-arabinofuranosyl)adenine 5'-monophosphate (Compound 19).

The compound was prepared, as its triethylammonium salt, as above from 9-(2-deoxy-2-fluoro-β-D-arabinofuranosyl)adenine (269 mg, 1 mmol) in 82% yield. $^{31}$P NMR (D$_2$O), δ 0.80 ppm, $^1$H NMR (D$_2$O), δ 1.22 (t, 9H, Et$_3$N), 3.12 (q, 6H, Et$_3$N), 4.02–4.06 (m, 2H, H5', H5"), 4.21 (q, 1H, H4', J$_{3',4}$=J$_{4',5'}$=J$_{4',5''}$=4.95 Hz), 4.69 (ddd, 1H, H3', J$_{2',3}$=4.4 Hz, J$_{3',F}$=19.0 Hz), 5.34 (dt, 1H, H2', J$_{2',F}$=51.7 Hz), 6.48 (dd, 1H, H1', J$_{1',2}$=4.4 Hz, J$_{1',F}$=14.5 Hz), 8.18 (s, 1H, H2), 8.48 (d, 1H, H8, J$_{8,F}$=2.1 Hz). Anal. (C$_{16}$H$_{28}$FN$_6$O$_6$P×3H$_2$O) C, H, N.

7. P$^1$-(Tiazofurin-5'-yl)-P$^2$-(2'-deoxy-2'-fluoroadenosin 5'-yl)pyrophosphate (Compound 3).

To a solution of Compound 10 (53 mg, 0.1 mmol) in DMF-d$_7$ (1 mL) was added the nucleotide Compound 11 (70 mg, 0.155 mmol, mono triethylammonium salt) and the mixture was kept at room temperature for 7 days. After that time, $^{31}$P NMR analysis showed a complete disappearance of the imidazolide Compound 10 resonance, the presence of the excess of Compound 11 (δ 2.39), and a group of signals at δ 9.15–9.75. The reaction mixture was then lyophilized and the residue was chromatographed by HPLC to give nucleotide Compound 11 (t$_R$=31.3 min., 26 mg), p$^1$,P$^2$-bis-(2'-deoxy-2'-fluoroadenosin-5'-yl)pyrophosphate (Compound 12) [t$_R$=35.1 min., 8 mg, $^1$H NMR (D$_2$O) δ 1.28 (t, 9H, Et$_3$N), 3.20 (q, 6H, Et$_3$N), 4.22–4.42 (m, 4H, 5',5"), 4.44–4.54 (m, 2H, H4') 4.57 (ddd, 2H, H3', J$_{3',F}$=21.5 Hz, J$_{2',3}$=3.4 Hz, J$_{3',4}$=7.8 Hz), 5.21 (dd, 2H, H2', J$_{2',F}$=52 2 Hz), 6.18 (d, 2H, H1', J$_{1',F}$=15.6 Hz), 8.03, 8.14 (two 2H singlets, H2, H8), $^{31}$P NMR (D$_2$O) δ–10.75, P$^1$-(2',3'-O-isopropylidenetiazofurin-5'-yl)-P$^2$-(2'-deoxy-2'-fluoroadenosin-5=-yl)pyrophosphate(Compound 14) (t$_R$= 43.7 min., 105 mg), and P$^1$,P$^2$-bis-(2',3'-O-isopropylidenetiazofurin-5'-yl)pyrophosphate (Compound 13) (t$_R$=51.2 min., 15 mg). Compounds 13 and 14 were deisopropylidenated by treatment with Dowex 50-X8 (H$^+$) in water overnight and purified by passing through a column of Dowex 50-X8 (H$^+$) to give dinucleotide Compound 15 (6 mg, 8.0%, the $^1$H NMR spectrum of this compound was identical with that of authentic sample$^{44}$) and Compound 3 (56 mg, 82%), respectively. TAD analogue Compound 3 was identical with that reported by us earlier$^{34}$. Compound 12 was also converted into free acids by passing through a column of Dowex 50-X8 (H+). The yield of Compound 12 was 5 mg (7.2%).

5 8. P$^1$-(Tiazofurin-5'-yl)-P$^2$-(3'-deoxy-3'-fluoroadenosin-5'-yl)pyrophosphate(Compound 4).

To a solution of 8 (53 mg, 0.1 mmol) in DMF-d$_7$ (1 mL) was added the 3'-deoxy-3'-fluoro-adenosine 5'-monophosphate (Compound 16, 70 mg, 0.155 mmol, mono triethylammonium salt) and the mixture was kept at room temperature for 10 days. The $^{31}$P NMR analysis showed a complete disappearance of the imidazolide Compound 10 resonance, presence of the excess of Compound 16 (δ 2.32), and the group of signals at δ–9.57 to δ–9.09. The reaction mixture was then lyophilized and the residue was applied on a preparative HPLC column to give nucleotide Compound 16 (t$_R$=30.6 min., 21 mg), P$^1$,P$^2$-bis-(3'-deoxy-3'-fluoroadenosin-5'-yl)pyrophosphate (Compound 17) (T$_R$= 34.8 min., 11 mg, $^1$H NMR (D$_2$O) δ 1.27 (t, 9H, Et$_3$N), 3.19 (q, 6H, Et$_3$N), 4.28 (pseudo s, 4H, 5',5"), 4.70 (d, 2H, H4', J$_{4',F}$=27.0 Hz), 4.82 (ddd, 2H, H2', J$_{2',F}$=27.0 Hz), 5.30 (dd, 2H, H3', J$_{3',F}$=54.0 Hz, J$_{2',3}$=4.25 Hz), 6.02 (d, 2H, H1', J$_{1',2}$=8.0 Hz), 8.05, 8.20 (two 2H singlets, H2, H8), $^{31}$P NMR (D$_2$O) δ–10.8], P$^1$-(2',3'-O-isopropylidene-tiazofurin-5'-yl)-P$^2$-(3'-deoxy-3'-fluoroadnosin-5'-yl)pyrophospate (Compound 18) (t$_R$=42.6 min., 98 mg), and P$^1$, P$^2$-bis-(2',3'-O-isopropylidenetiazofurin-5'-yl)pyrophosphate (Compound 13) (t$_R$=51.2 min., 13 mg). Compounds 13 and 18 were deisopropylidenated by treatment with Dowex 50-X8 (H$^+$) in water overnight and purified by passing through a column of Dowex 50-X8 (H$^+$) to give dinucleotide Compound 15 (5 mg, 7.5%) and TAD analogue Compound 4 (54 mg, 80%), respectively. Compound 4 $^{31}$P NMR (D$_2$O), δ–10.75 (brs), $^1$H NMR δ 4.21–4.34 [[m, 7H, H2'(T), H3'(T), H4'(T), H5'(T), H5"(T), H5'(A), H5"(A)], 4.68–74 [m, 1H, H4'(A)], 4.91–5.05 [m, 1H, H2'(A)], 5.09 [d, 1H, H1'(T), J$_{1',2}$=5.2 Hz], 5.36 [dd, 1H, H3'(A), J$_{2',F}$=53.5 Hz, J$_{2',3}$=4.2 Hz], 6.22 [d, 1H, H1'(A), J$_{1',2}$=7.9 Hz], 8.05 [s, 1H, H5(T)], 8.40 [s, 1H, H2(A)], 8.63 [s, 1H, H8 (A)]. Anal. (C$_{19}$H$_{24}$FN$_7$O$_{13}$P$_2$S×5H$_2$O) C, H, N.

Compound 17 was also converted into its free acid form by passing it through a column of Dowex 50-X8 (H$^+$). The yield of 15 was 4 mg (5.8 %). $^{31}$P NMR δ 10.75 (brs), $^1$H NMR (D$_2$O) δ4.27–4.31 (m, 3H, H4', H5', H5"), 4.7 (dt, 1H, H2', J$_{1',2}$=8.1 Hz, J$_{2',F}$=27.8 Hz, J$_{2',3}$=4.4 Hz), 5.30 (dd, 1H, H3', J$_{3',F}$=53.7 Hz), 6.03 (d, 1H, H1'), 8.06, 8.19 (two 1H singlets, H2, H8).

9. P$^1$-(Tiazofurin-5'-yl)-P$^2$-{[9-(2-deoxy-2-fluoro-β-D-arabinofuranosyl)adenine]-5'-yl)}pyrophosphate (Compound 5).

To the solution of Compound 10 (53 mg, 0.1 mmol)in DMF-d$_7$ (1 mL) was added the nucleotide Compound 19 (70 mg, 0.155 mmol., monotriethylammonium salt) and the mixture was kept at room temperature for 5 days. The $^{31}$P NMR analysis showed a complete disappearance of the imidazolide Compound 10 resonance and presence of the unreacted excess of Compound 19 at δ 2.45, and the group of signals at δ–9.82 to δ–9.36. The reaction mixture was lyophilized and the residue was purified by HPLC to give nucleotide Compound 19 (t$_R$=32.4 min., 27 mg), P$^1$, P$^2$-bis-{[9-(2-deoxy-2-fluoro-β-D-arabinofuranosyl)adenine]-5'-yl}pyrophosphate (Compound 20) (t$_R$=36.3 min., 10 mg, $^1$H NMR (D$_2$O) δ 1.28 (t, 9H Et$_3$N), 3.19 (q, 6H, Et$_3$N), 4.18–4.22 (m, 6H, 4',5',5"), 4.62 (dt, 2H, H3', J$_{3',F}$=18.35 Hz, J$_{2',3}$=3.8 Hz), 5.21 (dt, 2H, H2', J$_{2',F}$=51.7 Hz, J$_{1',2}$=4.0 Hz), 6.23 (dd, 2H, H1', J$_{1',F}$=14.0 Hz), 7.99, 8.17 (two 2H singlets, H2, H8), $^{31}$P NMR (D$_2$O) δ=–10.6], P$^1$-(2',3'-O-isopropylidenetiazofurin-5'-yl)-P$^1$-{[9-deoxy-2-fluoro-β-D-arabinofuranosyl)adenine]-5'-yl }pyrophospate (Compound 21) (t$_R$=43.3 min., 100 mg, $^{31}$P NMR δ–10.50 (P$^1$), –11.10 (P$^2$) AB system, J$_{P,P}$=21.3Hz; $^1$H NMR δ 1.22 (t, 18H, 2×Et$_3$N), 1.31 (s, 3H, iPr), 1.60 (s, 3H, iPr), 3.03 (q, 12H, 2×Et$_3$N), 4.08–4.12 [m, 2H, H5'(A), H5"(A)], 4.25–4.30 [m, 3H, H5'(T), H5"(T), H4'(A)], 4.44–4.47 [m, 1H, H4'(T)], 4.64–4.90 [m, 3H, H3'(A), H3'(T), H2'(T)], 5.14 [d, 1H, H1'(T), J$_{1',2}$=3.2 Hz], 5.35 [double pseudo t, 1H, H2'(A), J$_{2',F}$=51.8 Hz], 6.49 [dd, 1H, H1'(A), J$_{1',2}$=4.6 Hz, J$_{1',F}$=13.2 Hz], 8.08 [s, 1H, H5(T)], 8.18 [s, 1H, H2 (A)], 8.43 [d, 1H, H8 (A), J$_{8,F}$=1 Hz], and P$^1$,P$^2$-bis-(2',3'-O-isopropylidenetiazofurin-5'-yl)pyrophosphate (Compound 13) (t$_R$=51.3 min., 9 mg). Compound 21 was deisopropylidenated by treatment with Dowex 50-X8 (H$^{3O}$) in water overnight and purified by passing through a column of Dowex 50-X8 (H$^+$) to give dinucleotide 3 (51 mg, 76 %). $^{31}$P NMR δ–10.71 (brs), $^1$H NMR δ 4.21–4.34 [m, 8H, H2'(T), H3'(T), H4'(T), H5'(T), H5"(T), H4'(A), H5'(A), H5"(A)], 4.72 [two pseudo t, 1H, H3'(A), J$_{3',F}$=18.3 Hz], 5.09 [d, 1H, H1'(T), J$_{1',F}$=4.4 Hz], 5.37 [two pseudo t, 1H, H2'(A), J$_{2',F}$=51.7 Hz], 6.56 [dd, 1H, H1'(A), J$_{1',2}$=4.6 Hz, J$_{1',F}$=12.5 Hz], 8.05 [s, 1H, H5(T)], 8.40 [s, 1H, H2(A)], 8.52 [d; 1H, H8 (A), J$_{8,F}$=1.6 Hz]. Anal. (C$_{19}$H$_{24}$FN$_7$O$_{13}$P$_2$S×4H$_2$O) C, H, N.

TABLE 1
Scheme 1
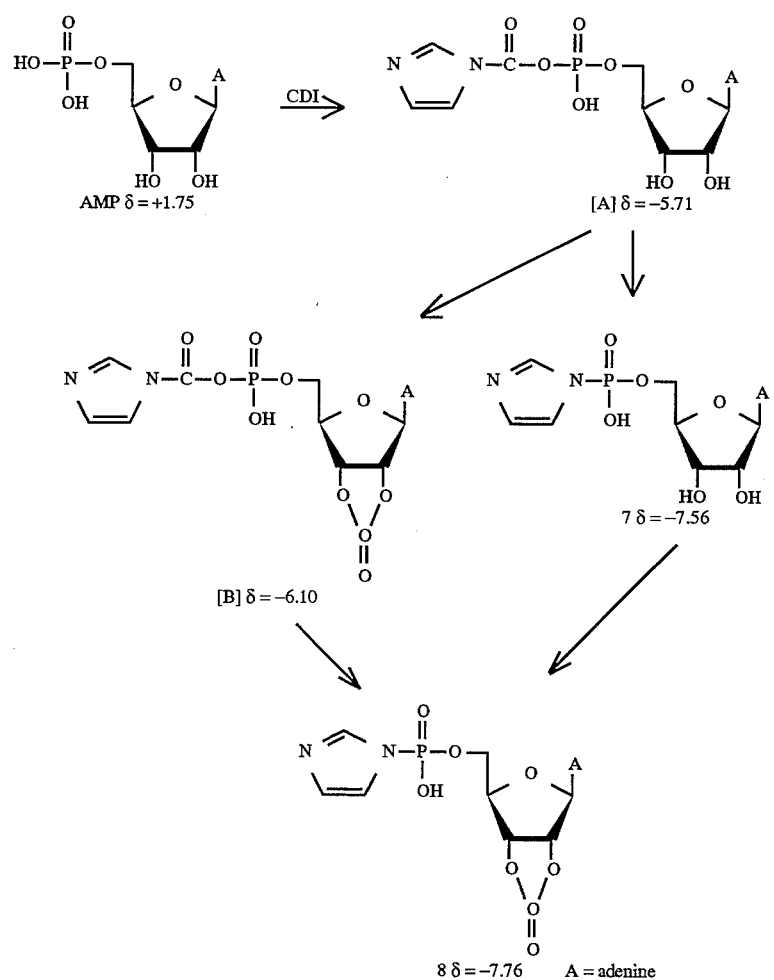
Scheme 2
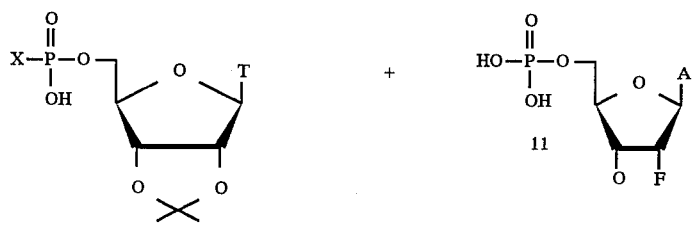

TABLE 1-continued
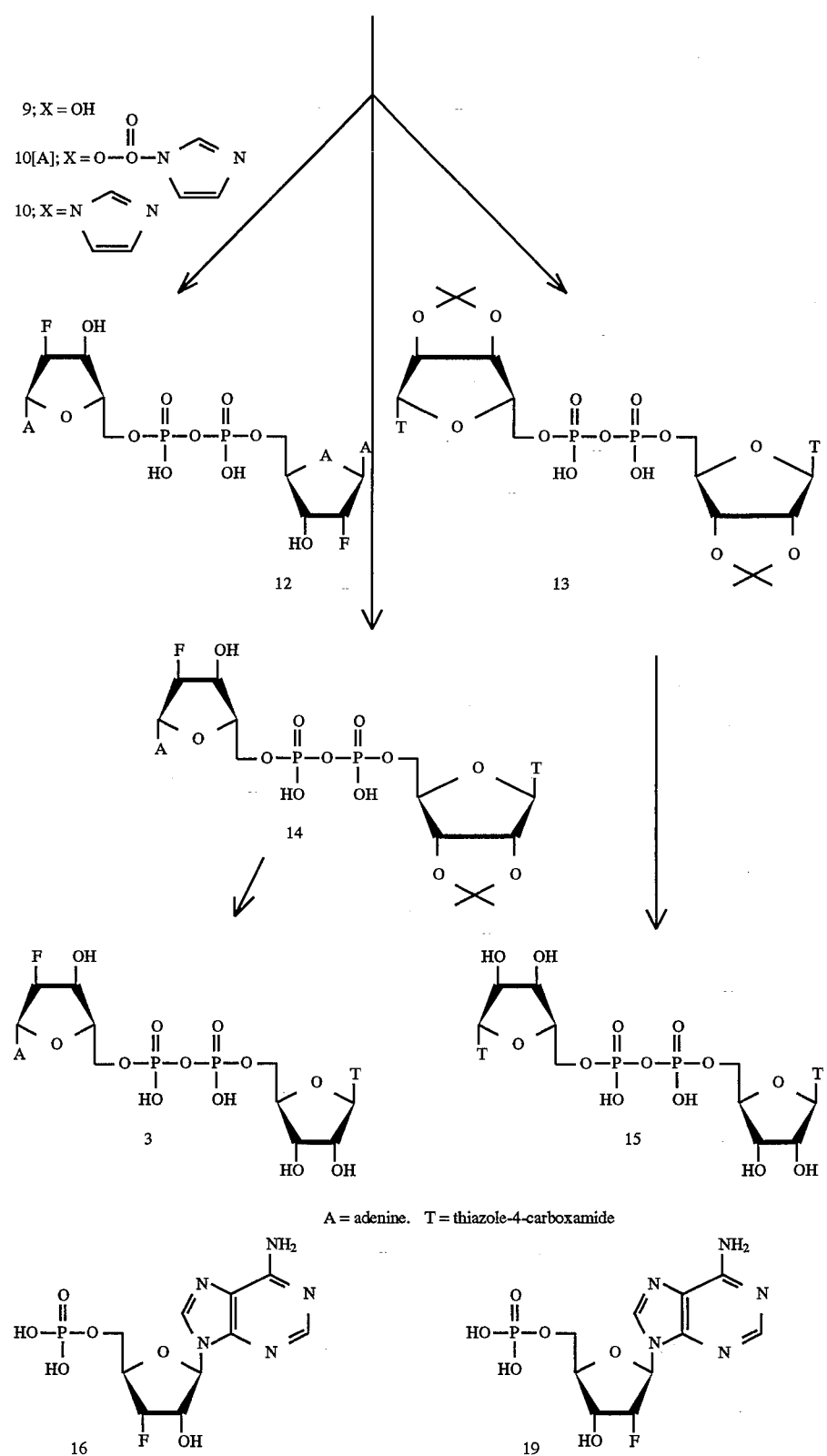

TABLE 1-continued

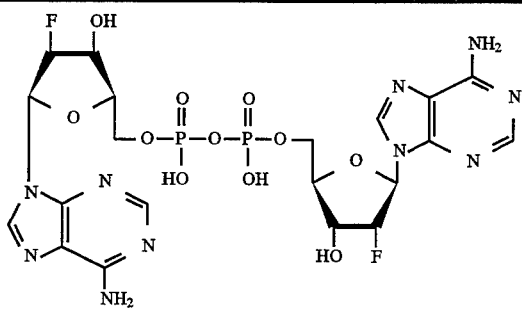

20

D. Results and Discussion

The fluoro substituted adenine nucleosides were prepared according to our recently developed simple method of direct introduction of a fluorine atom at C2' in the β-configuration of purine nucleosides (36,37) and efficient methods for the synthesis of 2'-deoxy-2'-fluoro-(34) and 3'-deoxy-3'-fluoroadenosine from adenosine (29) and were converted into their 5'-monophosphates by the Yoshikawa phosphorylation.(38)

Although the first successful synthesis of NAD was described by Todd (39) in 1957, a number of recent papers discuss different approaches to the chemical synthesis of dinucleotide pyrophosphates. Oppenheimer et al. (32) synthesized 2'-fluoroarabinose by the procedure developed in our laboratory (40), and then they synthesized 2'-fluoronicotinamide arabinoside 5'-monophosphate which was coupled with adenine mononucleotide (AMP). Using diphenylphosphorchloridate as the coupling agent according to Michelson's procedure (41), the desired dinucleotide was obtained in 22% yield. The same procedure gave only 9% yield in Slama's preparation of the carbocyclic NAD analogue. (42) The alternative coupling of adenosine 5'-(phosphoric-dibutyl-phosphinothioic) anhydride and carba-nicotinamide 5'-mononucleotide (Furusawa (43) ) afforded carbocyclic NAD in 50% yield. Finally, Marquez et al. (4,44) reported several different methods of preparation of TAD. Coupling of tiazofurin 5'-monophosphate (TRMP) with AMP in the presence of excess dicyclohexylcarbodiimide (DCC) gave only low yields of TAD. A 16% yield, which was attained when activated AMP was coupled with TRMP according to Furusawa's procedure, was also disappointing. Activation of AMP as its phosphoromorpholidate followed by reaction with TRMP afforded TAD in up to 31%, depending on the temperature and time of reaction. Although it was believed that, in the morpholidate route, no symmetrical side products were formed (since only one nucleotide was activated), the formation of $P^1,P^2$-diadenosine 5'-pyrophosphate (AppA) in amounts almost equal to TAD was observed. The authors (44) explained that traces of water hydrolyzed the activated AMP back to AMP which in turn would compete with TRMP for the remaining activated AMP.

The best results were achieved (44) by carbonyldiimidazole (CDI) activation (45) of TRMP and reaction in situ formed the 2',3'-carbonate derivative of the nucleotide imidazolide with AMP. The progress of the coupling reaction was followed by HPLC. In the same manner, several other NAD analogues were synthesized by these authors. The yields of isolated dinucleotides were generally in the range of 50%, and formation of AppA was not reported. Following Marquez's procedure, we have recently synthesized (34) the TAD analogue Compound 3 in 50% yield by CDI catalyzed coupling of TRMP with 2'-deoxy-2'-fluoroadenosine 5'-monophosphate (Compound 6).

We have shown above a simple and effective synthesis of NAD analogues (70–80% yield) by modification of the CDI catalyzed coupling reaction. We found that preparation of pure nucleotide imidazolides, known but never used used in coupling reactions, prior to the reaction with the corresponding nucleotides gave much better results than commonly used in situ generation (CDI) of the nucleotide imidazolides. The latter are sufficiently stable at about pH 7 for isolation by chromatographic purification.(45,46) Thus, we treated the commercially available AMP monohydrate with CDI (4 eq.) in $Me_2SO-d_6$ and followed the course of reaction (See Scheme 1 in Table 1) by $^{31}P$ (FIG. 1) and $^1H$ NMR. Immediately after addition of CDI, a complete disappearance of the resonance signal of Compound 6 (δ 1.75) and formation of intermediate [A] (δ–5.71) was observed in the $^{31}P$ NMR spectrum. The $^1H$ NMR of [A] (see Experimental Section) revealed a downfield shift of approximately 0.15 ppm for the H5" and the presence of three imidazolide protons at δ 6.99, 7.24, 7.48. After 20 minutes, the resonance signal of the intermediate [A] (70%) was still present but two new resonances, a singlet of intermediate [B] (16%) at δ–6.10 and another singlet of the AMP imidazolide (Compound 7, 14.5 %) at δ–7.76, were detected. After 1 hour the reaction mixture still contained [A] (7%), [B] (12%), and Compound 7 (26%) but formation of a significant amount of 2',3'-cyclic carbonate derivative Compound 8 (δ–7.75, 55%) was observed. Finally, all the reactants and intermediates disappeared and Compound 8 was the only product detected in the $^{31}P$ NMR spectrum of the reaction mixture (approximately 2 hours). HPLC purification of Compound 8 removed the excess imidazole but did not afford the pure AMP-imidazolide 2',3'-cyclic carbonate (Compound 8) due to its hydrolysis to AMP-imidazolide (Compound 7) in triethylammonium bicarbonate (TEAB) used as the eluent. Compounds 7 and 8 were well separated on the column but after work-up cyclic carbonate Compound 8 was always contaminated with unprotected imidazolide Compound 7. Therefore Compound 8 was treated with $Et_3N$-water to give pure imidazolide Compound 7 quantitatively. This compound was quite resistant to hydrolysis at neutral pH. Even traces of AMP were undetectable in a sample of Compound 7 which was kept in water solution at room temperature for more than 2 weeks.

Since the nucleotide imidazolide 2',3'-cyclic carbonates were not stable enough for HPLC purification, we synthesized the acetonide protected tiazofurin 5'-phosphorimidazolide (Compound 10, Table 1 Scheme 2) for further (NMR monitored) reaction with our fluoro substituted adenosine nucleotides. Thus, treatment of 2',3'-O-isopropylidenetiazofurin 5'-monophosphate (4,44,47) (Compound 9) with CDI (1.1 eq.) in DMF-d$_7$ at room temperature for 1 hour afforded the imidazolide Compound 10 in quantitative yield. Again, the corresponding intermediate [A] was formed first and then was converted into the desired imidazolide Compound 10 as judged by $^{31}$P NMR (disappearance of signal at δ 1.63 and appearance of the resonance peak of [A] at δ−6.53, which vanished with time with simultaneous formation of the final peak of Compound 10 at δ−7.79). Imidazolide Compound 10 was isolated by lyophilization of the reaction mixture and then separated from the excess imidazole by preparative HPLC, and isolated as the triethylammonium salt, which was stable in neutral and alkaline conditions. Compound 19 was then dissolved in DMF-d$_7$ and allowed to react with nucleotide Compound 11 (34) (1.5 eq., as mono-triethylammonium salt) at room temperature. After 7 days, the $^{31}$P NMR analysis showed the disappearance of imidazolide Compound 10 singlet and formation of a major group of resonance signals at δ 9.15–9.76. The resonance signal of unreacted Compound 11 (20 %) was also detected at δ 2.39. After lyophilization, the residue was chromatographed on a HPLC column to give nucleotide Compound 11 (26 mg), $P^1,P^2$-bis-(2'-deoxy-2'-fluoroadenosin-5'-yl) pyrophosphate (Compound 12, 8 mg), $P^1$-(2',3'-O-isopropylidenetiazofurin-5'-yl)-$P^2$-(2'-deoxy-2'-fluoroadenosin-5'-yl) pyrophosphate (Compound 14, 105 mg) and $P^1,P^2$-bis-(2',3'-O-isopropylidenetiazofurin-5'-yl) pyrophosphate (Compound 13, 15 mg). Treatment of Compounds 13 and 14 with Dowex 50W-X8 (H$^+$) in water gave the dinucleotide Compound 15 (44) and the desired TAD analog Compound 3, respectively. The overall yield of Compound 3 was 56 mg (82%).

Reaction of 3'-deoxy-3'-fluoroadenosine 5'-monophosphate Compound 16 with tiazofurin imidazolide derivative Compound 10 required 11 days for completion, affording the TAD analogue Compound 4 in 80% yield. Again the symmetrical pyrophosphate derivatives, namely the $P^1,P^2$-bis-(3'-deoxy-3'-fluoroadenosin-5'-yl) pyrophosphate Compound 17 and bis-tiazofurin pyrophosphate derivative Compound 13 were obtained in 6% and 5% yield, respectively.

In a similar manner, the 9-(2-deoxy-2-fluoro-β-D-arabinofuranosyl) adenine 5'-monophosphate Compound 19 was converted (5 days) into the corresponding TAD analogue Compound 5 in 76% yield. The symmetrical dinucleotide Compound 20 (6%) and ditiazofurin pyrophosphate Compound 13 (5%) were also isolated.

Finally, we studied the possibility of imidazolide activation of our fluoro substituted nucleotides Compounds 11, 16, and 19, and subsequent coupling of these imidazolides with TRMP. Although a such procedure did not require any protection to avoid formation of 2',3'-cyclic carbonates in reaction with CDI and further coupling was equally efficient, we encountered serious difficulties in HPLC separation of unprotected TAD analogues from symmetrical dinucleotides (AppA-analogues and TRppTR). The procedure with acetonide protected TRMP was found to be most efficient.

Since the "activated" nucleotide Compound 7 was found to be resistant to hydrolysis in water, disproportionation of unsymmetrical dinucleotides rather than hydrolysis of the imidazolides was apparently responsible for the formation of symmetrical pyrophospates. The low yields of coupling reactions reported in the literature were probably due to poor control of reaction conditions in in situ generated reacting species.

EXAMPLE 10

Biological Activity-Inhibition of IMPDH type II and LADH.

Purified human recombinant IMPDH-II was obtained from Dr. George D. Markham of the Institute for Cancer Research, Fox Chase Cancer Center, Fox Chase, Pa. Horse liver ADH was obtained in crystalline form from Boehringer Mannheim Biochemicals, Indianapolis. β-Nicotinamide adenine dinucleotide (NAD) in crystalline free acid form was also obtained from Boehringer. Inosine 5'-monophosphate (IMP) was purchased from Sigma Chemical Co., St. Louis as the disodium salt. All solutions were prepared using nano-pure water.

Kinetic constants of the inhibitors with respect to NAD were obtained by monitoring spectrophotometrically the rate of production of NADH during the reaction. The course of the reaction was followed by measuring the changing absorbance of the reaction mixture at 340 nm, the absorbance peak for NADH, using a Beckman DU-65 spectrophotometer, and an extinction of 6.22 A mM$^{-1}$ cm$^{-1}$ for the reduced cofactor.(51)

Human IMPDH type II was stored at −70° C. in buffer containing 20 mM KCl, 1 mM EDTA, 1 mM DTT and 20 mM Tris-HCl adjusted to pH 8 at 23° C. In preparation for the assays, a frozen aliquot was thawed rapidly and filtered through a 0.45 μm acetate filter. Protein concentration was determined from a Coomassie Assay. In some cases the enzyme was diluted 4:1 in similar 20 mM Tris buffer. NAD and IMP solutions were prepared based on molecular weight. The IMP concentration at the beginning of each run was kept at 100 μM, approximately ten times the published $K_m$ for IMPDH.(14)

Combination of the reactants was performed as follows: An aliquot of substrate solution was pipetted down one side of a cuvet, one of co-factor down another side, and inhibitor down a third. The volume was brought to 990 μL with reaction buffer and the cuvet was agitated. This mixture was allowed to incubate in the spectrophotometer sample holder for five minutes before the reaction was started, the temperature held at 37° C. by a circulating water bath. The reaction was initiated by the introduction of 10 μL of enzyme solution on a mixing plunger, and NADH production was monitored for between two and 10 minutes, depending on the activity of the protein solution.

The uninhibited rate of reaction as a function of cofactor concentration was first established. Velocities at four NAD concentrations and saturating substrate concentrations were measured and $K_m$ for NAD obtained. Inhibitor was then introduced to the reaction mixture with an NAD concentration in the vicinity of $K_m$. The initial trial concentration of inhibitor was 100 μM. If no reaction was observed, the inhibitor solution underwent serial 10:1 dilutions until reasonable velocities were obtained.

Once a range of inhibitor concentrations resulting in measurable velocities was established, runs were performed with NAD concentrations of 20, 40, 80, and 160 μM, with two or three inhibitor concentrations. Lineweaver-Burk plots were used to assess the quality of the data and to initially characterize the mode of inhibition with respect to NAD. However, values of inhibition constants and patterns of inhibition were ultimately obtained by direct least-squares fits to the nonreciprocal forms of the Michaelis-Menten rate equation.(52) The pattern of inhibition considered to best account for the observed data was that giving both the smallest residuals between observed and calculated values, and the smallest standard errors in the computed kinetics constants. Data for all compounds tested were most consistent with a noncompetitive pattern of inhibition of IMPDH-II with respect to NAD at saturating IMP concentrations. Consequently, values of $k_{ii}$ (intercept) and $k_{is}$ (slope) reported in Table I were obtained from direct least squares fits to the expression:

$$v_o=V_m[A]/\{K_m(1+[I]/K_{is})+[A](1+[I]/K_{ii})\}$$

where $v_o$ is the measured initial rate, $V_m$ is the maximum rate, $K_m$ is the Michaelis constant of NAD, and [A] is concentration of NAD.

Preliminary assays of alcohol dehydrogenase were performed in a similar manner to that described above. LADH in crystalline suspension was spun down to a pellet and dissolved in 100 mM Tris-HCl buffer containing 100 mM KCl adjusted to pH 8 at 23° C. Stock solutions of NAD and ethanol were prepared in buffer based on molecular weight and volume, respectively. Ethanol was introduced as an aliquot of stock solution and its concentration was kept constant at 1.2 mM while NAD concentration was varied by serial dilution of the stock solution. If the initial trial concentration did not influence the velocity measurably, larger amounts of inhibitor were used to established at least a lower bound for $k_i$, given the limited amounts of inhibitors available.

Results and Discussion

Inhibition of inosine monophosphate dehydrogenase type II (IMPDH-type II), by the fluorinated TAD analogues Compounds 3, 4, and 5, and by the parent compound TAD and the phosphodiesterase resistant analogues β-CH$_2$-TAD and S-CF$_2$-TAD were examined. As noted IMPDH-type II is the target isozyme, predominant in neoplastic cells.(15,16) be bound by any theory, these findings suggest either the presence of the key electrophilic residues at the adenine pocket, and/or sufficient flexibility in this site to adopt to functional changes at the adenine end of the inhibitor. This flexibility is apparently not present in LADH, whose site is dominated by the nucleophilic Asp 223. (18,23) These findings indicate that the newly synthesized compounds are potent inhibitors of IMPDH-II, show selectivity, and are of therapeutic interest.

TABLE 2

Inhibition of Human IMPDH type II by TAD analogues.
NAD is the variable substrate, with IMP constant at 100 μM.
The pattern of inhibition in each case is non-competitive. Values were obtained at 37° C..

| Inhibitor | $K_{ii}$ (μM) | $K_{is}$ (μM) |
|---|---|---|
| 13 | 0.5 ± 0.1 | 6.0 ± 12.0 |
| 24 | 0.7 ± 0.1 | 1.5 ± 0.6 |
| 35 | 2.9 ± 0.5 | 13. ± 10. |
| β-CF$_2$-TAD | 0.17 ± 0.03 | 0.3 ± 0.2 |
| β-CH$_2$-TAD | 0.11 ± 0.02 | 0.2 ± 0.1 |
| TAD | 0.19 ± 0.03 | 0.3 ± 0.1 |
| NADH | 120. ± 7. | 175. ± 22. |

TABLE 3

Analyses

| Compound | Formula | Analyses Calculated C | H | N | Found C | H | N |
|---|---|---|---|---|---|---|---|
| 2 4 × 5H$_2$O | C$_{19}$H$_{24}$FN$_7$O$_{13}$P$_2$S × 5H$_2$O | 29.97 | 4.50 | 12.88 | 29.67 | 4.27 | 12.80 |
| 3 5 × 4H$_2$O | C$_{19}$H$_{24}$FN$_7$O$_{13}$P$_2$S × 4H$_2$O | 30.69 | 4.24 | 13.19 | 30.92 | 4.60 | 13.68 |
| 9 11 × Et$_3$N × 3H$_2$O | C$_{16}$H$_{28}$FN$_6$O$_6$P × 3H$_2$O | 38.40 | 6.79 | 16.66 | 38.21 | 6.32 | 16.78 |
| 14 16 × Et$_3$N × 3H$_2$O | C$_{16}$H$_{28}$FN$_6$O$_6$P × 3H$_2$O | " | " | " | 38.47 | 6.41 | 16.80 |
| 17 19 × Et$_3$N × 3H$_2$O | C$_{16}$H$_{28}$FN$_6$O$_6$P × 3H$_2$O | " | " | " | 38.53 | 6.66 | 16.88 |

Interestingly, all the fluorinated compounds showed good inhibitory activity against IMPDH-type II, generally binding in the $10^{-7}$ molar range (Table 2). The pattern of inhibition with respect to NAD is noncompetitive in each case. Like type I, IMPDH-type II follows an ordered Bi—Bi mechanism, the binding of substrate preceding that of cofactor.(14) Thus, this pattern of inhibition is consistent with binding of the inhibitors to both free enzyme and to the enzyme-substrate complex.(48)

In most cases, binding is tighter than or comparable to that seen for binding of TAD to human IMPDH-II (Table 2), as well as to IMPDH from variety of sources. (4,8,12,22) Binding of β-CF$_2$-TAD is equivalent to that of both TAD and the phosphorodiesterase resistant analogue β-CH$_2$-TAD (33), itself a biologically effective inhibitor.(9) Compounds 3–5 showed similar affinity, the ara-fluorinated derivative Compound 5 showing the weakest binding. However, in all cases, binding is significantly tighter than that of NADH.

The results suggest that fluorine substituents can effectively mimic the functional role of the hydroxyl group in IMPDH-II. Displacement of this functionality to the 2'-ara-position of the sugar is less successful, although still surprisingly effective in this enzyme. Although not wishing to

REFERENCES

1. NAD analogues 4. For Part 3, see Zatorski, A.; Lipka, P.; Pankiewicz, K. W. Collect. Czech. Chem. Commun., 1993, 58, 122–126.
2. Cooney, D. A.; Jayaram, H. N.; Gebeyehu, G.; Betts, C. R.; Kelly, J. A.; Marquez, V. E.; Johns, D. G. Biochem. Pharmacol., 1982, 31, 2133–2136.
3. Kuttan, R.; Robins, R. K.; Saunders, P. P. Biochem. Biophys. Res. Commun., 1982, 107, 862–868.
4. Gebeyehu, G.; Marquez, V. E.; Kelly, J. A.; Cooney, D. A.; Jayaram, H. N.; Johns, D. G. J. Med. Chem., 1983, 26, 922–925.
5. Robins, R. K.; Srivastava, P. C.; Narayanan, V. L.; Plowman, J.; Paull, K. D. 2-β-D-Thiazole-4-carboxamide, a Novel Potential Antitumor Agent for Lung Tumors and Metastases. J. Med. Chem., 1982, 25, 107–108.
6. Earle, M. F; Glazer, R. I. Activity and Metabolism of 2-β-D-Ribofuranosylthiazole-4-carboxamide in Human Lymphoid Tumor Cells in Culture. Cancer Res., 43 (1983) 133–137.
7. Ahluwalia, G. S.; Cooney, D. A.; Marquez, V. E.; Jayaram, H. N.; Johns, D. G. Studies on the Mechanism of Action of Tiazofurin (2-β-D-Ribofuranosylthiazole-4-carboxamide). *Biochem. Pharmacol.*, 1986, 35, 3783–3790.

8. Cooney, D. A.; Jayaram, H. N.; Glazer, R. A.; Kelly, J. A.; Marquez, V. E.; Gebeyehu, G.; van Cott, A. C.; Zwelling, L. A.; Johns, D. G. Studies on the mechanism of action of tiazofurin metabolism to an analog of NAD with potent IMP dehydrogenase-inhibitory activity. *Adv. Enzyme Regul.*, 1983, 21, 271–303.

9. Goldstein, B. M.; Leary, J. F.; Farley, B. A.; Marquez, V. E.; Levy, P. C.; Rowley, P. T. Induction of HL60 Cell Differentiation by Tiazofurin and Its Analogues. *Blood.*, 1991, 78, 593–598.

10. Robins, R. K. Nucleoside and Nucleotide Inhibitors of Inosine Monophosphate (IMP) Dehydrogenase as Potential Antitumor inhibitors. *Nucleosides & Nucleotides*, 1982, 1, 35–44.

11. Collart, F. R.; Chubb, C. B.; Mirkin, B. L.; Huberman, E. Increased Inosine-5'-phosphate Dehydrogenase Gene Expression in Solid Tumor Tissues and Tumor Cell Lines. *Cancer Res.*, 1992, 52, 5826–5828.

12. Yamada, Y.; Natsumeda, Y.; Weber, G. Action of the Active Metabolites of Tiazofurin and Ribavirin on Purified IMP Dehydrogenase. *Biochemistry*, 1988, 27, 2193–2196.

13. Goldstein, B. M.; Ellis Bell, J.; Marquez, V. E. Dehydrogenase Binding by Tiazofurin Anabolites. *J. Med. Chem.*, 1990, 33, 1123–1127.

14. Carr, S. F.; Papp, E.; Wu, J. C.; Natsumeda, Y. Characterization of Human Type I and Type II IMP Dehydrogenases. *J. Biol. Chem.*, 1993, 268, 27286–27290.

15. Nagai, M.; Natsumeda, Y.; Konno, Y.; Hoffman, R.; Irino, S.; Weber, G. Selective Up-Regulation of Type II 5'-Monophosphate Dehydrogenase Messenger RNA Expression in Human Leukemias. *Cancer Res.*, 1991, 51, 3886–3890.

16. Nagai, M.; Natsumeda, N.; Weber, G. Proliferation-linked Regulation of Type II IMP Dehydrogenase Gene in Human Normal Lymphocytes and HL-60 Leukemic Cells. *Cancer Res.*, 1992, 52, 258–261.

17. Grau, W. M. Structural Interactions with Enzymes. In *The Pyridine Nucleotide Coenzymes*, Anderson, B. M., Everse, J., You, K.-S., Eds.; Academic Press: New York, 1982; pp 135–187.

18. Eklund, H., Branden, C. I. Crystal Structure, Coenzyme Conformations, and Protein Interactions. In *Pyridine Nucleotide Coenzymes*, Part A, Dolphin, D., Avramovic, O., Poulson, R., Eds.; Wiley & Sons; New York, 1987; pp 74–85.

19. Woenckhaus, C., Jeck, R. Preparation and Properties of NAD and NADP Analogs. In *Pyridine Nucleotide Coenzymes*, Part A, Dolphin, D., Avramovic, O., Poulson, R., Eds.; Wiley & Sons; New York, 1987;pp 533–540.

20. Li, H.; Hallows, W. A.; Punzi, J. S.; Marquez, V. E.; Carrel, H. L.; Pankiewicz, K. W.; Watanabe, K. A.; Goldstein, B. M. Crystallographic Studies of Two Alcohol Dehydrogenase-Bound Analogs of Thiazole-4-carboxamide Adenine Dinucleotide (TAD), the Active Anabolite of the Antitumor Agent Tiazofurin. *Biochemistry*, 1994, 33, 23–32.

21. Eklund, H., Branden, C.-I. In *Biological Macromolecules and Assemblies. Active Sites of Enzymes*, Vol. 3: Jurnak, F. A., McPherson, A. Eds.; John Wiley and Sons, New York, 1987, chapter 2.

22. Hedstrom, L.; Wang, C. C. Mycophenotic Acid and Thiazole Adenine Dinucleotide Inhibition of *Tritrichomonas foetus* Inosine 5'-monophosphate Dehydrogenase: Implication on Enzyme Mechanism. *Biochemistry*, 1990, 29, 849–854.

23. Bergstrom, D. E., Swartling, D. J. Fluorine Substituted Analogs of Nucleic Acid Components. In *Fluorine Containing Molecules, Structure, Reactivity, Synthesis, and Applications*, Liebman, J. F., Greenberg, A., Dolbier, Jr., W. R., Eds.; VCH Publishers, Inc.: New York, 1988; pp 259–308.

24. Uesugi, S.; Miki, M. Ikehara, H. Iwahashi, Y. Kyogoku. A Linear Relationship Between Electronegativity of 2'-Substitutents and Conformation of Adenine Nucleosides. *Tetrahedron Lett.*, 1979, 4073–4076.

25. Stoeckler, J. D.; Bell, C. A.; Parks, Jr., R. E.; Chu, C. K.; Fox, J. J.; Ikehara, M. C(2')-Substituted Purine Nucleoside Analogs. *Biochem. Pharmacol.*, 1982, 31, 1723–1728.

26. Ishihama, A.; Enami, M.; Nishijama, Y.; Fukui, T.; Otsuka, E.; Ikehara, M. 2'-Deoxy-2'-azidoadenosine triphosphate and 2'-deoxy-2'-fluoroadenosine triphosphate as substrates and inhibitors for *Escherichia coli* DNA-dependent RNA polymerase. *J. Biochem.*, 1980, 87, 825–830.

27. Uesugi, S.; Kaneyasu, T.; Matsugi.; Ikehara, M. Improved Synthesis of 2'-Fluoro-2'-Deoxyadenosine and Synthesis and Carbon-13 NMR Spectrum of Its 3',5'-Cyclic Phosphate Derivative. *Nucleosides & Nucleotides*, 1983, 2, 373–385.

28. Koide, S.; Yokoyama, S.; Matsuzawa, H.; Miyazawa, T.; Ohta, T. Conformation of $NAD^+$ Bound to Allosteric L-Lactate Dehydrogenase Activated by Chemical Modification. *J. Biol. Chem.*, 1989, 264, 8676–8679.

29. Pankiewicz, K. W.; Krzeminski, J.; Watanabe, K. A. Synthesis of 2'-β-Fluoro-and 3'-α-Fluoro-Substituted Guanine Nucleosides. Effects of Sugar Conformational Shifts on Nucleophilic Displacement of the 2'-Hydroxy and 3'-Hydroxy Group with DAST. *J. Org. Chem.*, 1992, 57, 7315–7321 and references therein.

30. Van Aerschot, A.; Herdewijn, P.; Janssen, G.; Cools, M.; De Clercq, E. Synthesis and Antiviral Activity Evaluation of 3'-Fluoro-3'-deoxyribonucleosides: Broad-Spectrum Antiviral Activity of 3'-Fluoro-3'-deoxyadenosine. *Antiviral Res.*, 1989, 12, 133–150.

31. Pankiewicz, K. W.; Krzeminski, J.; Ciszewski, L. A.; Ren, W.-Y.; Watanabe, K. A. A synthesis of 9-(2-Deoxy-2-fluoro-β-D-arabinofuranosyl) adenine and Hypoxanthine. An Effect of C3'-Endo to C2'-Endo Conformational Shift on the Reaction Course of 2'-Hydroxyl Group with DAST. *J. Org. Chem.*, 1992, 57, 553–559.

32. Sleath, P. R.; Handlon, A. L.; Oppenheimer, N. J. Pyridine Coenzyme Analogues. 3. Synthesis of Three $NAD^+$ Analogues Containing a 2'-Deoxy-2'-substituted Nicotinamide Arabinofuranosyl Moiety. *J. Org. Chem.*, 1991, 56, 3608–3613.

33. Marquez, V. E.; Tseng, C. K. H.; Gebeyehu, G.; Cooney, D. A.; Ahluwalia, G. S.; Kelly, J. A.; Dalal, M.; Fuller, R. W.; Wilson, Y. A.; Johns, D. G. Thiazole-4-carboxamide Adenine Dinucleotide (TAD). Analogues Stable to Phosphodiesterase Hydrolysis. *J. Med. Chem.*, 1986, 29, 1726–1731.

34. Zatorski, A.; Lipka, P.; Mollova, N.; Schram, K. H.; Goldstein, B. M.; Watanabe, K. A.; Pankiewicz, K. W. Synthesis of Thiazole-4-carboxamide Adenine Difluoromethylenediphosphonates Substituted with Fluorine at C-2'of the Adenosine. *Carbohydr. Res.*, 1993, 249, 95–108.

35. Jayaram, H. N.—personal communication. 36. Pankiewicz, K. W., Watanabe, K. W. A Synthesis of 2'-Fluoro-and 3'-Fluoro-Substituted Purine Nucleosides via Direct Approach. In *Nucleosides and Nucleotides as*

*Antitumor and Antiviral Agents*, Chu, C. K., Baker, D. C., Eds.; Plenum Press: New York, 1993; pp 55–71.

37. Pankiewicz, K. W.; Watanabe, K. A. Synthesis of 2'-β-Fluoro-Substituted Nucleosides by a Direct Approach. *J. Fluor. Chem.*, 1993, 64, 14–36.

38. Yoshikawa, M.; Kato, T.; Takenishi, T. A Novel Method for Phosphorylation of Nucleosides to 5'-Nucleotides. *Tetrahedron Lett.*, 1967, 50, 5065–5068.

39. Hughes, N. N.; Kenner, G. W.; Todd, A. R. Codehydrogenase III. Synthesis of diphosphopyridine nucleotide (cozymase) and triphosphopyridine nucleotide. *J. Chem. Soc.*, 1957, 3733–3738.

40. Reichman, U.; Watanabe, K. A.; Fox, J. J. A Practical Synthesis of 2-Deoxy-2-Fluoro-D-Arabinofuranose Derivatives. *Carbohydr. Res.*, 1975, 42, 233–240.

41. Michelson, A. M. Polynucleotide and nucleotide coenzymes. *Biochim. Biophys. Acta.* 1964, 91, 1.

42. Slama, J. T.; Simmons, A. M. Carbanicotinamide Adenine Dinucleotide: Synthesis and Enzymological Properties of a Carbocyclic Analogue of Oxidized Nicotinamide Adenine Dinucleotide. *Biochemistry*, 1988, 27, 183–193.

43. Furusawa, K.; Sekine, M.; Hata, T. Studies on Pyrophosphates. Part III. A New Method for the Synthesis of Nucleotide Coenzymes by Means of Di-n-butylphosphinothioyl Bromide. *J. Chem. Soc. Perkin I*, 1976, 1711–1716.

44. Gebeyehu, G.; Marquez, V. E.; Van Cott, A.; Cooney, D. A.; Kelley, J. A.; Jayaram, H. N.; Ahluwalia, G. S.; Dion, R. L.; Wilson, Y. A.; Johns, D. G. Ribavirin, Tiazofurin, and Selenazofurin: Mononucleotides and Nicotinamide Adenine Dinucleotide Analogues. Synthesis, Structure, and Interactions with IMP Dehydrogenase. *J. Med. Chem.*, 1985, 28, 99–105.

45. Cramer, F.; Neunhoeffer, H. Reaktionen yon Adenosin-5'-phosphorsaure-imidazolidiene neue Synthese von Adenosinphosphat und Flavin-adenin-dinucleotid. *Chem. Ber.*, 1962, 95, 1664–1669.

46. Scheit, K. H. In Nucleotide Analogs. Synthesis and Biological Function, John Wiley and Sons: New York, 1980; p. 214.

47. In our hands, the phosphorylation of 2',3'-O-isopropylidenetiazofurin (iPrTR) under Yoshikawa procedure gave somewhat different result than that described previously.(4) We did not observe deisopropylidenation in reaction of iPrTR with P(O)C₃ as reported, but instead dehydration of amide function took place. Thus, after HPLC separation we obtained the desired 2',3'-O-isopropylidenetiazofurin 5'--monophosphate (Compound 9) in 50% yield and the 2-(2,3-O-isopropylidene-β-D-ribofuranosyl)thiazole-4-carbonitrile 5'-monophosphate (Compound 9a) in 30 % yield. For $^1$H, $^{13}$C, and $^{31}$P NMR of Compound 9 and its carbonitrile derivative Compound 9a, see Experimental Details section.

48. Segel, I. H.; In Enzyme Kinetics, Behavior and Analysis of *Rapid Equilibrium and Steady-State Enzyme Systems*. Wiley & Sons: New York, 1975; pp.560.

49. Although the nucleotide Compound 11 was synthesized in 1983 by Ikehara et al.(27), the full description of its $^1$H NMR spectra has been never published. It is worthy to note that all resonances of Compound 11, except for H4', are well resolved in the spectrum. The H4' resonance is expected to appear as ddd due to coupling with H3' H5', and H5" but instead was recorded as multiplet. This is due to long range coupling with phosphorus. Simulation of this spin system with estimated value of $J_{4',P}=1.2$ Hz afforded the spectrum containing the original H4' multiplet.

50. The long range coupling of the fluorine with H5'($J_{5',F}=$ 1.2 Hz) resulted in the presence of the H5' multiplet in the simulated $^1$H NMR spectrum of Compound 16. Similarly, the multiplet resonance of H4' was due to the coupling of H4' with the phosphorus with estimated coupling constant $J_{4',P}=1.8$ Hz.

51. Kaplan, N. O. The Pyridine Coenzymes. In *The Enzymes*, Vol. III, 2nd ed.; Boyer, P. D., Lardy, H., Myrback, K., Eds.; Academic Press: New York, 1960; pp. 105–169.

52. Cleland, W. W. Statistical Analysis of Enzyme Kinetics Data. *Methods Enzymol*, 1979, 63, 103–109.

What is claimed is:

1. A compound having the structure:

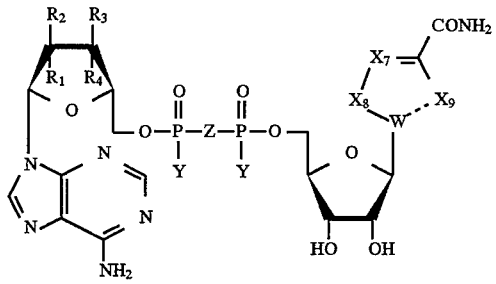

wherein each $R_1$, $R_2$, $R_3$, and $R_4$ is independently fluorine, OH or H; Z is O, $CH_2$ or $CF_2$; each Y is independently OH or F; $X_7$ is N or CH, $X_8$ is NH; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH.

2. A compound having the structure:

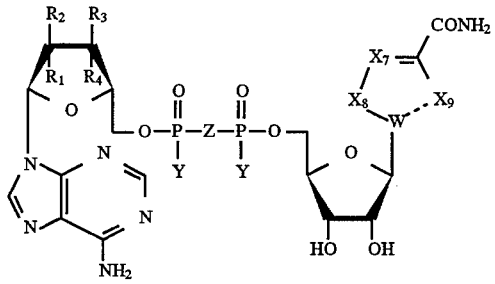

wherein one of $R_1$, $R_2$, $R_3$, and $R_4$ is fluorine, one is OH and the remainder are H; Z is O, $CH_2$ or $CF_2$; each Y is independently OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH.

3. The compound of claim 2 having the structure:

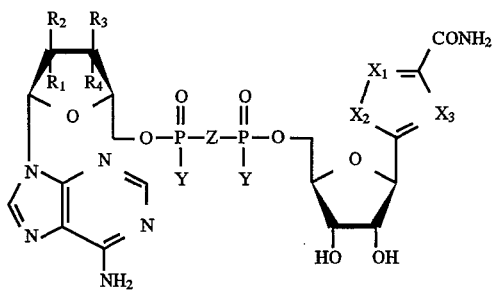

wherein one of $R_1$, $R_2$, $R_3$, and $R_4$ is fluorine, one is OH and the remainder are H; Z is O, $CH_2$ or $CF_2$; each Y is independently OH or F; $X_1$ is N or CH, $X_2$ is NH, S or Se; and $X_3$ is N or CH.

4. The compound of claim 2 having the structure:

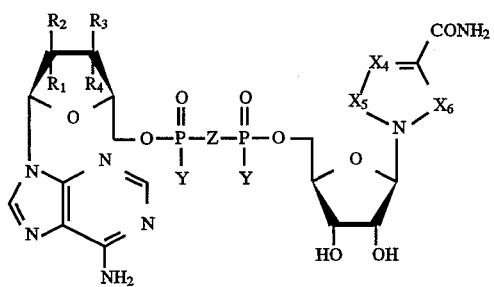

wherein one of $R_1$, $R_2$, $R_3$, and $R_4$ is fluorine, one is OH and the remainder are H; Z is O, $CH_2$ or $CF_2$; each Y is independently OH or F; $X_4$ is N or CH, $X_5$ is NH, S or Se; and $X_6$ is NH, CH, S or Se.

5. A compound having the structure:

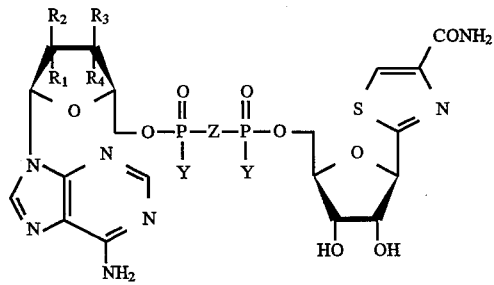

wherein one of $R_1$, $R_2$, $R_3$, and $R_4$ is fluorine, one is OH and the remainder are H; each Y is independently F or OH, and Z is O, $CH_2$ or $CF_2$.

6. The compound of claim 5 having the structure:

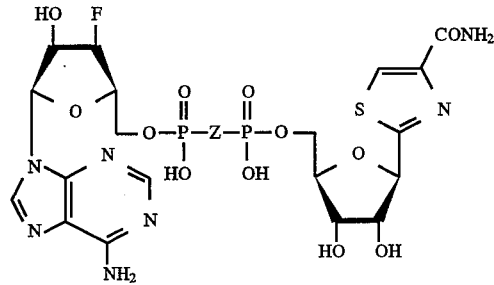

wherein each Y is independently F or OH, and Z is O, $CH_2$ or $CF_2$.

7. The compound of claim 5 having the structure:

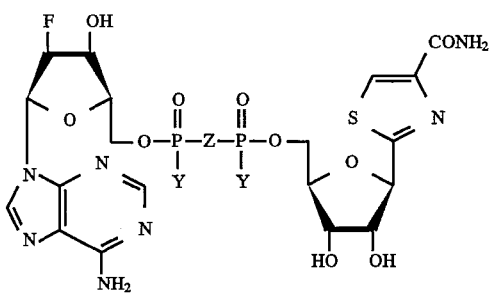

wherein each Y is independently F or OH, and Z is O, $CH_2$ or $CF_2$.

8. The compound of claim 5 having the structure:

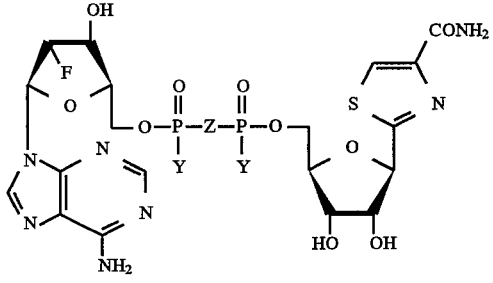

wherein each Y is independently F or OH, and Z is O, $CH_2$ or $CF_2$.

9. A compound having the structure:

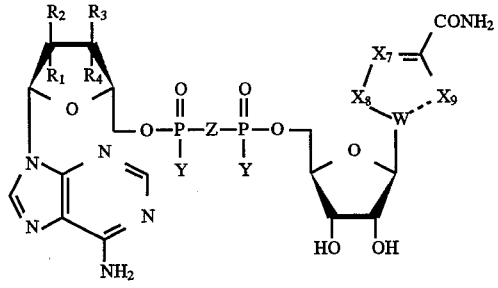

wherein each $R_1$, $R_2$, $R_3$, and $R_4$ is independently fluorine, OH or H; Z is $CH_2$ or $CF_2$; each Y is independently OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH.

10. A compound having the structure:

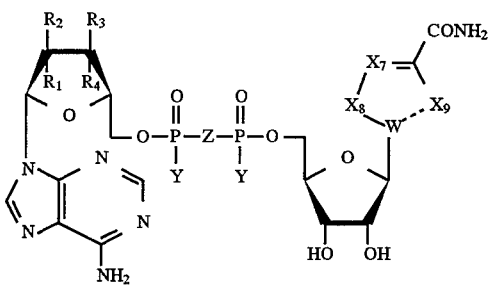

wherein each $R_1$, $R_2$, $R_3$, and $R_4$ is independently fluorine, OH or H; Z is O, $CH_2$ or $CF_2$; wherein one Y is F and the other Y is either OH or F; $X_7$ is N or CH, $X_8$ is NH, S or Se; and W is C or N, wherein when W is C, the dashed line (---) represents a double bond and $X_9$ is N or CH, and wherein when W is N, the dashed line (---) represents a single bond and $X_9$ is S or Se, or the dashed line (---) represents a double bond and $X_9$ is N or CH.

11. A compound having the structure:

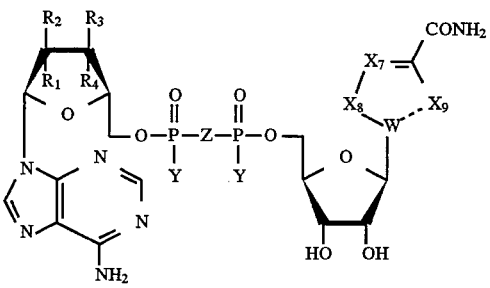

wherein each $R_1$, $R_2$, $R_3$, and $R_4$ is independently fluorine, OH or H; Z is O, $CH_2$ or $CF_2$; each Y is independently OH or F; $X_7$ is N or CH, $X_8$ is NH, S or Se; and W is N, the dashed line (---) represents a single bond and $X_9$ is S or Se.

12. A pharmaceutical composition which comprises a compound of claim 1, 2, 4, 9, 10 or 11 and a pharmaceutically acceptable carrier.

13. A method of treating a mammal having an inosine monophosphate dehydrogenase associated disorder which comprises administering to the mammal, a therapeutically effective amount of a compound of claim 9.

14. A method of treating a mammal having an inosine monophosphate dehydrogenase associated disorder which comprises administering to the mammal a therapeutically effective amount of a compound of claim 10.

15. A method of treating a mammal having an inosine monophosphate dehydrogenase associated disorder which comprises administering to the mammal a therapeutically effective amount of a compound of claim 11.

16. A method of treating a mammal having an inosine monophosphate dehydrogenase associated disorder which comprises administering to the mammal a therapeutically effective amount of a compound of claim 1.

17. A method of treating a mammal having an inosine monophosphate dehydrogenase associated disorder which comprises administering to the mammal a therapeutically effective amount of a compound of claim 2.

18. A method of treating a mammal having an inosine monophosphate dehydrogenase associated disorder which comprises administering to the mammal a therapeutically effective amount of a compound of claim 4.

19. The method of claim 13, 14, 15, 16, 17 or 18 wherein the disorder is characterized by the proliferation of malignant cells.

20. The method of claim 13, 14, 15, 16, 17 or 18 wherein the disorder is a leukemia.

21. The method of claim 13, 14, 15, 16, 17 or 18 wherein the disorder is a cancer.

* * * * *